(12) United States Patent
Dalton et al.

(10) Patent No.: US 6,676,944 B2
(45) Date of Patent: Jan. 13, 2004

(54) VACCINE CONTAINING A PEROXIREDOXIN AND/OR A β-TUBULIN

(75) Inventors: John Pius Dalton, Orpen Grove (IE); Stuart John Andrews, Staines (GB)

(73) Assignee: John P. Dalton, Dublin (IE)

( * ) Notice: Subject to any disclaimer, the term of this patent is extended or adjusted under 35 U.S.C. 154(b) by 0 days.

(21) Appl. No.: 09/202,329

(22) PCT Filed: Jun. 11, 1997

(86) PCT No.: PCT/GB97/01573

§ 371 (c)(1),
(2), (4) Date: Feb. 19, 1999

(87) PCT Pub. No.: WO97/47740

PCT Pub. Date: Dec. 18, 1997

(65) Prior Publication Data

US 2003/0124137 A1 Jul. 3, 2003

(30) Foreign Application Priority Data

Jun. 11, 1996 (GB) .............................................. 9612214

(51) Int. Cl.⁷ ............................................ A61K 39/00
(52) U.S. Cl. ............................... 424/191.1; 424/184.1; 424/185.1; 424/193.1; 424/265.1; 530/300; 530/333; 530/350
(58) Field of Search .................... 424/184.1, 185.1, 424/191.1, 265.1, 143.1; 530/300, 333, 350

(56) References Cited

U.S. PATENT DOCUMENTS 5,610,286 A * 3/1997 Shau et al.

FOREIGN PATENT DOCUMENTS

| WO | 9008819 | 8/1990 |
|---|---|---|
| WO | 9409142 | 4/1994 |
| WO | 9428925 | 12/1994 |
| WO | 9610583 | 4/1996 |

OTHER PUBLICATIONS

Stitt et al. Parasitology Research. 1992. 78: 103–107.*
Ohno et al. PIR62 Accession No. P20749, 1990.*
Ahmad et al. PIR62 Accession No. S18457, 1991.*
Sullivan et al. PIR62 Accession No. A24701, 1986.*
Lewis et al. Swiss–prot38 Accession No. P05217, 1985.*
Chae et al. PIR62 Accession No. A57716, 1994.*
Chae et al., *Proc. Natl. Acad. Sci. USA*, vol. 91, 1994, pp. 7017–7021.
Blaxter et al., *Mol. Biochem. Parasitol.*, vol. 77, Apr. 1996, pp. 77–93.
McGonigle et al., *Parasitology*, vol. 115, No. 1, Jul. 1997, pp. 101–104.
Blaxter et al., EMBL, database entry OV400; accession No. R95400;.

* cited by examiner

Primary Examiner—Jennifer E. Graser
(74) Attorney, Agent, or Firm—Rothwell, Figg, Ernst & Manbeck

(57) ABSTRACT

Vaccine compositions comprising peroxiredoxin and/or β-tubulin antigenic material, preferably of Fasciola or Dicrocoelium origin, for use in combating a parasitic infestation of helminths in a mammal, are provided. Also provided are nucleic acid sequences which encode peroxiredoxin and/or β-tubulin molecules and the amino acid sequences thereof, vectors comprising said nucleic acid sequences and cells transformed with such vectors.

2 Claims, 11 Drawing Sheets

| | 10 20 30 40 50 |
|---|---|
| 2E 1- 50 clone D6<br>11 1- 49 | CGGTNCCANT NCCCCNANCC CGGTANTTAA CCGGATTCCC ANANTGCCCC<br>  G  ?   ?    ?   ?  ?   P V  ?  N   R  I  P   ?   ?  P |
| | 60 70 80 90 100 |
| 2E 51-100 clone D6<br>11 50- 99 | AAAANGNGCC CNCCCCNGAA TAAAATTCCT NAANNCNCNN GNTGGCCCAN<br>  Q  ?   ?  P  ?   ?  E   O  N  S  ?  ?  ?  ?   ?  A  ? |
| | 110 120 130 140 150 |
| 2E 101-150 clone D6<br>11 100-149 | TTACCAACCC NNGAAACCNA NAAATNTGGG GNNCCTNAGG GNCCCCAGAA<br>  L  P  T   ?  E  T   ?  K   ?  G    ?  P  ?   ?  P  Q  N |
| | 160 170 180 190 200 |
| 2E 151-200 clone D6<br>11 150-199 | CTNACACCAA NAAATTTTNA ANCCAANAAA CNNANGGCCC CCTTTTGAAC<br>  ?  H  Q   ?  I  ?   ?  P  ?  N   ?  ?  P   P  F  E |
| | 210 220 230 240 250 |
| 2E 201-250 clone D6<br>11 200-249 | CCACTCATGG GCGCCTAACT TAAGGTGGCC GCCCTGTTCC GNGGTCGAAT<br>  P  T  H  G  R  L  T   O  G  G   R  P  V  P   ?  S  N |
| | 260 270 280 290 300 |
| 2E 251-300 clone D6<br>11 250-299 | GTCCCATGAA ANAAGTGGAC GAACAGATGC TGAATGTGCA GNAACAAAGA<br>  V  P  J   ?  K  W  T   N  R  C   J  M  C    ?  N  K  E |
| | 310 320 330 340 350 |
| 2E 301-350 clone D6<br>11 300-349 | ATTCCAAGCT ACTTTGTCGA ATGGNATCCC GAATAACGTG AAAACTGCGG<br>  F  Q  A   T  L  S   N  ?  I  P   N  N  V   K  T  A |
| | 360 370 380 390 400 |
| 2E 351-400 clone D6<br>11 350-399 | TTTGTGACAT TCCACCTAGG GGCCTTAAAA TGTCGGTCAC ATTTGTTGGC<br>  V  C  D  I   P  P  R   G  L  K   M  S  V  T   F  V  G |

FIG.2A

| | |
|---|---|
| | 410        420        430        440        450 |
| 2E 401-450 clone D6<br>11   400-449 | AATAGTACTG CCATACAAGA ACTATTCAAA CGTGTCTCCG AGCAGTTCAC<br> N  S  T    A  I  Q   E   L   F   K    R  V   S    E   Q   F   T |
| | 460        470        480        490        500 |
| 2E 451-500 clone D6<br>11   450-499 | CGCAATGTTC CGTCGCAAAG CATTCTTGCA TTGGTACACA GGCGAAGGTA<br>  A  M   F    R  R   K    A   F   L    H   W   Y   T    G   E   G |
| | 510        520        530        540        550 |
| 2E 501-550 clone D6<br>11   500-549 | TGGACGAGAT GGAGTTCACC GAGGCCGAAT CGAACATGAA CGATCTGGTC<br> M  D   E   M    E   F   T    E   A   E    S   N   M   N    D   L   V |
| | 560        570        580        590        600 |
| 2E 551-600 clone D6<br>11   550-599 | AGTGAATATC AGCAATACCA AGANGCAACC GCTGAGGAGG AAGGCGAATT<br> S  E   Y    Q  Q   Y   Q    ?   A   T    A  E   E    E   G   E   F |
| | 610        620        630        640        650 |
| 2E 601-650 clone D6<br>11   600-649 | CCAGCTGANC GCCGGCGCTA CCATTACCAG TTGGTCTGGT GTCAAATCCC<br> Q  L   ?    A  G   A    T   I   T    S   W   S   G    V   K   S |
| | 660        670        680        690        700 |
| 2E 651-700 clone D6<br>11   650-699 | AGCATGGCGC CGGAGCATCG ACGNNGCCCA ATCGCCCTNN GTAGCCGNTTA<br> Q  H   G    A  G   A   S    T   ?   P    N   R   P    ?    B    ?   L |

FIG.2B

```
clone D6              1   -------------------------------------------------G
β Tubulin Toxoplasma  1   MREIVHVQGGQCGNQIGAKFWEVISDEHGIDPTG clone D6              1   -------------------------------------------------L
β Tubulin Toxoplasma  35  TYCGDSDLQLERINVFYNEATGGRFVPRAILMDL clone D6              1   -------------------------------------------------A
β Tubulin Toxoplasma  69  EPGTMDSVRAGPFGQLFRPDNFVFGQTGAGNNWA clone D6              1   -------------------------------------------------T
β Tubulin Toxoplasma  103 KGHYTEGAELIDSVLDVVRKEAEGCDCLQGFQIT clone D6              1   -------------------------------------------------F
β Tubulin Toxoplasma  137 HSLGGGTGSGMGTLLISKVREEYPDRIMETFSVF clone D6              1   -------------------------------------------------N
β Tubulin Toxoplasma  171 PSPKVSDTVVEPYNATLSVHQLVENADEVQVIDN clone D6              1   -------------------------------------------------T
β Tubulin Toxoplasma  205 EALYDICFRTLKLTTPT-YGDLNHLVSAAMSGVT
```

FIG.3A

```
clone D6          1    ----------------------------------------------------------------  -
β Tubulin Toxoplasma  238  CCLRFPGQLNSDLRKLAVNLVPFPRLHFFLIGFA clone D6          1    ----------------------------------------------------------------  -
β Tubulin Toxoplasma  272  PLTSRGSQQYRALSVPELTQQMFDAKNMMCASDP clone D6          1    ------------RCJMCZNKEF----QATLSNZ
β Tubulin Toxoplasma  306  RHGRYLTASAMFRGRMSTKEVDEQMLNVQNKNSS clone D6         18    ---IPNNVKTAVCDIPPRGLKMSVTFVGNSTAI
β Tubulin Toxoplasma  340  YFVEWIPNNMKSSVCDIPPKGLKMSVTFVGNSTA clone D6         48    QELFKRVSEQFTAMFRRKAFLHWYTGEGMDEMEF
β Tubulin Toxoplasma  374  IQEMFKRVSDQFTAMFRRKAFLHWYTGEGMDEME clone D6         82    TEAESNMNDLVSEYQQYQZATAEEEGEFQLZAGA
β Tubulin Toxoplasma  408  FTEAESNMNDLVSEYQQYQDATAEEGEFDEEEG clone D6        116    TITSWSGVKSQHGAGASTZPNRPZBZL
β Tubulin Toxoplasma  442  EMGAEEGA-------------------
```

FIG.3B

Nucleotide sequence and predicted amino acid sequence of clone B1 containing the peroxiredoxin gene

```
-178                   TCGCTCACTATAGGGCGAATTGGGCCCGACGTCGCAT
-141 GCCCCCGGCCGCCATGGCCGCGGGATTGGTGGCGACGACTCCTGGA
 -95 GCCCGTNAGTATCAGCGGAATTCCGGTGTGATCGCAATCAGTGCTCTC
 -47 CGGGGCGCCATCCACTTCCCCACTCTCATCCGCATTTCCAAAGACCG
```

```
  1  ATG TTG CAG CCT AAT ATG CCC GCC CCG AAT TTT TCT GGA
     met leu gln pro asn met pro ala pro asn phe ser gly   (12)
 40  CAG GCG GTA GTG GGC AAG GAG TTC GAA ACC ATC AGT TTA
     gln ala val val gly lys glu phe glu thr ile ser leu   (25)
 79  TCA GAC TAC AAG GGC AAA TGG GTG ATT CTC GCC TTC TAT
     ser asp tyr lys gly lys trp val ile leu ala phe tyr   (38)
118  CCA CTT GAT TTC ACG TTC GTG TGT CCA ACG GAA ATA ATC
     pro leu asp phe thr phe val cys pro thr glu ile ile   (51)
157  GCG ATC AGT GAT CAG ATG GAG CAG TTC GCA CAA CGT AAC
     ala ile ser asp gln met glu gln phe ala gln arg asn   (64)
196  TGC GCC GTC ATC TTC TGC TCT ACT GAC TCG GTT TAT TCG
     cys ala val ile phe cys ser thr asp ser val tyr ser   (77)
235  CAT CTG CAA TGG ACC AAA ATG GAT CGT AAG GTT GGC GGT
     his leu gln trp thr lys met asp arg lys val gly gly   (90)
274  ATA GGC CAG CTG AAC TTC CCG CTG CTG GCA GAC AAG AAT
     ile gly gln leu asn phe pro leu leu ala asp lys asn   (103)
313  ATG TCT GTC TCT CGC GCC TTT GGT GTT CTG GAT GAG GAA
     met ser val ser arg ala phe gly val leu asp glu glu   (116)
352  CAG GGT AAT ACC TAC CGT GGC AAT TTC CTC ATC GAT CCC
     gln gly asn thr tyr arg gly asn phe leu ile asp pro   (129)
391  AAG GGG GTC CTG CGC CAG ATC ACG GTG AAT GAC GAC CCG
     lys gly val leu arg gln ile thr val asn asp asp pro   (142)
430  GTG GGC CGT TCC GTT GAA GAA GCC TTG CGT CTG CTC GAT
     val gly arg ser val glu glu ala leu arg leu leu asp   (155)
469  GCA TTC ATA TTC CAC GAG GAG CAT GGA GAG GTC TGC CCG
     ala phe ile phe his glu glu his gly glu val cys pro   (168)
508  GCG AAC TGG AAG CCT AAA AGC AAG ACC ATC GTG CCT ACT
     ala asn trp lys pro lys ser lys thr ile val pro thr   (181)
547  CCG GAT GGA TCC AAA GCA TAT TTC TCC TCA GCC AAC TAG
     pro asp gly ser lys ala tyr phe ser ser ala asn ***   (193)
```

```
586 TGAACAAGGGTGCTTAATCCCGGCTCTGTGTTTCGTTTCTGGTTTAAAA
635 TAAATTAGATAATACGGTGCAAAAAAAAAAAAAAAAAACGGAATNCCGGT
684 ACGGTAACAGTTCCCAAGCGCAACAGTATGATGAGAATCCAACTGATTA
733 TCGTCTTGGAATCGCTCATTGGTTTCGCAACCAGTTTTCGACTGNAGGC
782 AACCGCATTCAAGGATTGTGGCTCGCAACTTGCCGAATTGATGAATGTG
831 ACTGTGAAACCATGTGANACTACTCTGTGTACTGNGTNTCGNGGNCANA
880 ACGCCCAACTGGAAATCACTTCCCGAACAAAGGAAGTTGGCAAGTCTTG
929 AAAGCAGTCGGCCCGTNCAATAGTCGGACGTGTTTCTGCCCATCCCCCT
978 GGATGACTA
```

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| clone B1 | 102 | D | K | N | M | S | V | S | R | A | F | G | V | L | D | E | E | Q | G | N | T | Y | R | G | N | F | L | I | D | P | K | G | V | L | R Q I |
| TSA rat | 106 | D | V | T | K | S | L | S | Q | N | Y | G | V | L | K | N | D | E | G | I | A | Y | R | G | L | F | I | I | D | A | K | G | V | L | R Q I |
| NKFB human | 104 | D | V | T | R | R | L | S | E | D | Y | G | V | L | K | T | D | D | E | G | I | A | Y | R | G | L | F | I | I | D | G | K | G | V | L | R Q I |
| PAG human | 107 | D | P | K | R | T | I | A | Q | D | Y | G | V | L | K | K | A | D | D | E | G | I | S | F | R | G | L | F | I | I | D | D | K | G | V | L | R Q I |
| TSA human | 106 | D | V | T | R | R | L | S | E | D | Y | G | V | L | K | N | D | E | G | I | A | Y | R | G | L | F | I | I | D | G | K | G | V | L | R Q I |
| TSA Oncocherca | 109 | V | V | D | S | L | Q | L | T | A | V | K | L | V | A | T | P | V | D | W | K | D | G | D | D | C | V | V | L | P | T | I | D | D | N E A |

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| clone B1 | 138 | T | V | N | D | D | P | V | G | R | S | V | E | E | A | L | R | L | L | D | A | F | I | F | H | E | E | H | G | E | V | C | P | A | N W K |
| TSA rat | 142 | T | V | N | D | L | P | V | G | R | S | V | D | D | E | A | L | R | L | V | Q | A | A | F | Q | Y | T | D | E | H | G | E | V | C | P | A G W K |
| NKFB human | 140 | T | V | N | D | L | P | V | G | R | S | V | D | D | E | A | L | R | L | V | Q | A | F | Q | F | T | D | K | H | G | E | V | C | P | A G W K |
| PAG human | 143 | T | V | N | D | L | P | V | G | R | S | V | D | E | T | L | R | L | V | Q | A | F | Q | F | T | D | E | H | G | E | V | C | P | A G W K |
| TSA human | 142 | T | V | N | D | L | P | V | G | R | S | V | D | E | A | L | R | L | V | Q | A | F | Q | F | T | D | E | H | G | E | V | C | P | A A W K |
| TSA Oncocherca | 145 | K | K | L | F | G | E | K | I | H | T | I | D | L | P | S | G | K | – | – | – | – | – | – | – | – | – | – | – | – | – | – | – | – | – |

| | | | | | | | | | | | | | | | | | | |
|---|---|---|---|---|---|---|---|---|---|---|---|---|---|---|---|---|---|---|
| clone B1 | 174 | P | K | S | K | T | I | V | P | T | P | D | G | S | K | A | Y | F | S S A N |
| TSA rat | 178 | P | G | S | D | T | I | K | P | N | V | D | D | D | S | K | E | Y | F S K H N |
| NKFB human | 176 | P | G | S | D | T | I | K | P | N | V | D | D | S | S | K | E | Y | F S K H N |
| PAG human | 179 | P | G | S | D | T | I | K | P | D | V | Q | K | S | K | E | Y | F S K Q K |
| TSA human | 178 | P | G | R | D | T | I | K | P | N | V | D | D | S | S | K | E | Y | F S K H N E |
| TSA Oncocherca | 0 | – | – | – | – | – | – | – | – | – | – | – | – | – | – | – | – | – | – |

FIG.5B

SEQUENCE LISTING

```
<160> NUMBER OF SEQ ID NOS: 21

<210> SEQ ID NO 1
<211> LENGTH: 700
<212> TYPE: DNA
<213> ORGANISM: Fasciola hepatica
<220> FEATURE:
<221> NAME/KEY: CDS
<222> LOCATION: (2)..(700)
<220> FEATURE:
<221> NAME/KEY: unsure
<222> LOCATION: (5)
<223> OTHER INFORMATION: n = a, or t, or c, or g
<220> FEATURE:
<221> NAME/KEY: unsure
<222> LOCATION: (9)
<223> OTHER INFORMATION: n=a or t or c or g
<220> FEATURE:
<221> NAME/KEY: unsure
<222> LOCATION: (11)
<223> OTHER INFORMATION: n= a or t or c or g
<220> FEATURE:
<221> NAME/KEY: unsure
<222> LOCATION: (18)
<223> OTHER INFORMATION: n= a or t or c or g
<220> FEATURE:
<221> NAME/KEY: unsure
<222> LOCATION: (16)
<223> OTHER INFORMATION: n= a or t or c or g
<220> FEATURE:
<221> NAME/KEY: unsure
<222> LOCATION: (26)
<223> OTHER INFORMATION: n= a or t or c or g
<220> FEATURE:
<221> NAME/KEY: unsure
```

```
<222> LOCATION: (42)
<223> OTHER INFORMATION: n= a or t or c or g
<220> FEATURE:
<221> NAME/KEY: unsure
<222> LOCATION: (44)
<223> OTHER INFORMATION: n= a or t or c or g
<220> FEATURE:
<221> NAME/KEY: unsure
<222> LOCATION: (55)
<223> OTHER INFORMATION: n = a or t or c or g
<220> FEATURE:
<221> NAME/KEY: unsure
<222> LOCATION: (57)
<223> OTHER INFORMATION: n= a or t or c or g
<220> FEATURE:
<221> NAME/KEY: unsure
<222> LOCATION: (62)
<223> OTHER INFORMATION: n= a or t or c or g
<220> FEATURE:
<221> NAME/KEY: unsure
<222> LOCATION: (67)
<223> OTHER INFORMATION: n = a or t or c or g
<220> FEATURE:
<221> NAME/KEY: unsure
<222> LOCATION: (81)
<223> OTHER INFORMATION: n = a or t or c or g
<220> FEATURE:
<221> NAME/KEY: unsure
<222> LOCATION: (84)..(85)
<223> OTHER INFORMATION: n= a or t or c or g
<220> FEATURE:
<221> NAME/KEY: unsure
<222> LOCATION: (87)
<223> OTHER INFORMATION: n= a or t or c or g
<220> FEATURE:
<221> NAME/KEY: unsure
<222> LOCATION: (89)..(90)
<223> OTHER INFORMATION: n = a or t or c or g
<220> FEATURE:
<221> NAME/KEY: unsure
<222> LOCATION: (92)
<223> OTHER INFORMATION: n= a or t or c or g
<220> FEATURE:
<221> NAME/KEY: unsure
<222> LOCATION: (100)
<223> OTHER INFORMATION: n= a or t or c or g
<220> FEATURE:
<221> NAME/KEY: unsure
<222> LOCATION: (111)..(112)
<223> OTHER INFORMATION: n = a or t or c or g
<220> FEATURE:
<221> NAME/KEY: unsure
<222> LOCATION: (119)
<223> OTHER INFORMATION: n = a or t or c or g
<220> FEATURE:
<221> NAME/KEY: unsure
<222> LOCATION: (121)
<223> OTHER INFORMATION: n = a or t or c or g
<220> FEATURE:
<221> NAME/KEY: unsure
<222> LOCATION: (126)
<223> OTHER INFORMATION: n = a or t or c or g
<220> FEATURE:
<221> NAME/KEY: unsure
<222> LOCATION: (132)..(133)
<223> OTHER INFORMATION: n = a or t or c or g
<220> FEATURE:
<221> NAME/KEY: unsure
<222> LOCATION: (137)
<223> OTHER INFORMATION: n= a or t or c or g
<220> FEATURE:
<221> NAME/KEY: unsure
<222> LOCATION: (142)
<223> OTHER INFORMATION: n = a or t or c or g
<220> FEATURE:
<221> NAME/KEY: unsure
<222> LOCATION: (153)
<223> OTHER INFORMATION: n = a or t or c or g
<220> FEATURE:
```

```
<221> NAME/KEY: unsure
<222> LOCATION: (161)
<223> OTHER INFORMATION: n = a or t or c or g
<220> FEATURE:
<221> NAME/KEY: unsure
<222> LOCATION: (169)
<223> OTHER INFORMATION: n = a or t or c or g
<220> FEATURE:
<221> NAME/KEY: unsure
<222> LOCATION: (172)
<223> OTHER INFORMATION: n = a or t or c or g
<220> FEATURE:
<221> NAME/KEY: unsure
<222> LOCATION: (177)
<223> OTHER INFORMATION: n= a or t or c or g
<220> FEATURE:
<221> NAME/KEY: unsure
<222> LOCATION: (182)..(183)
<223> OTHER INFORMATION: n= a or t or c or g
<220> FEATURE:
<221> NAME/KEY: unsure
<222> LOCATION: (185)
<223> OTHER INFORMATION: n = a or t or c or g
<220> FEATURE:
<221> NAME/KEY: unsure
<222> LOCATION: (242)
<223> OTHER INFORMATION: n = a or t or c or g
<220> FEATURE:
<221> NAME/KEY: unsure
<222> LOCATION: (262)
<223> OTHER INFORMATION: n = a or t or c or g
<220> FEATURE:
<221> NAME/KEY: unsure
<222> LOCATION: (292)
<223> OTHER INFORMATION: n = a or t or c or g
<220> FEATURE:
<221> NAME/KEY: unsure
<222> LOCATION: (325)
<223> OTHER INFORMATION: n = a or t or c or g
<220> FEATURE:
<221> NAME/KEY: unsure
<222> LOCATION: (574)
<223> OTHER INFORMATION: n = a or t or c or g
<220> FEATURE:
<221> NAME/KEY: unsure
<222> LOCATION: (609)
<223> OTHER INFORMATION: n = a or t or c or g
<220> FEATURE:
<221> NAME/KEY: unsure
<222> LOCATION: (674)..(675)
<223> OTHER INFORMATION: n = a or t or c or g
<220> FEATURE:
<221> NAME/KEY: unsure
<222> LOCATION: (689)..(690)
<223> OTHER INFORMATION: n = a or t or c or g
<220> FEATURE:
<221> NAME/KEY: unsure
<222> LOCATION: (697)
<223> OTHER INFORMATION: n = a or t or c or g
<220> FEATURE:
<221> NAME/KEY: unsure
<222> LOCATION: (2)..(4)
<223> OTHER INFORMATION: Xaa = unknown
<220> FEATURE:
<221> NAME/KEY: unsure
<222> LOCATION: (6)
<223> OTHER INFORMATION: Xaa = unknown
<220> FEATURE:
<221> NAME/KEY: unsure
<222> LOCATION: (9)
<223> OTHER INFORMATION: Xaa = unknown
<220> FEATURE:
<221> NAME/KEY: unsure
<222> LOCATION: (14)..(15)
<223> OTHER INFORMATION: Xaa = unknown
<220> FEATURE:
<221> NAME/KEY: unsure
<222> LOCATION: (18)..(19)
<223> OTHER INFORMATION: Xaa = unknown
```

```
<220> FEATURE:
<221> NAME/KEY: unsure
<222> LOCATION: (21)
<223> OTHER INFORMATION: Xaa = unknown
<220> FEATURE:
<221> NAME/KEY: unsure
<222> LOCATION: (27)..(31)
<223> OTHER INFORMATION: Xaa = unknown
<220> FEATURE:
<221> NAME/KEY: unsure
<222> LOCATION: (33)
<223> OTHER INFORMATION: Xaa = unknown
<220> FEATURE:
<221> NAME/KEY: unsure
<222> LOCATION: (37)
<223> OTHER INFORMATION: Xaa = unknown
<220> FEATURE:
<221> NAME/KEY: unsure
<222> LOCATION: (40)
<223> OTHER INFORMATION: Xaa = unknown
<220> FEATURE:
<221> NAME/KEY: unsure
<222> LOCATION: (42)
<223> OTHER INFORMATION: Xaa = unknown
<220> FEATURE:
<221> NAME/KEY: unsure
<222> LOCATION: (44)
<223> OTHER INFORMATION: Xaa = unknown
<220> FEATURE:
<221> NAME/KEY: unsure
<222> LOCATION: (46)..(47)
<223> OTHER INFORMATION: Xaa = unknown
<220> FEATURE:
<221> NAME/KEY: unsure
<222> LOCATION: (51)
<223> OTHER INFORMATION: Xaa = unknown
<220> FEATURE:
<221> NAME/KEY: unsure
<222> LOCATION: (54)
<223> OTHER INFORMATION: Xaa = unknown
<220> FEATURE:
<221> NAME/KEY: unsure
<222> LOCATION: (56)..(57)
<223> OTHER INFORMATION: Xaa = unknown
<220> FEATURE:
<221> NAME/KEY: unsure
<222> LOCATION: (59)
<223> OTHER INFORMATION: Xaa = unknown
<220> FEATURE:
<221> NAME/KEY: unsure
<222> LOCATION: (61)..(62)
<223> OTHER INFORMATION: Xaa = unknown
<220> FEATURE:
<221> NAME/KEY: unsure
<222> LOCATION: (81)
<223> OTHER INFORMATION: Xaa = unknown
<220> FEATURE:
<221> NAME/KEY: unsure
<222> LOCATION: (87)
<223> OTHER INFORMATION: Xaa = unknown
<220> FEATURE:
<221> NAME/KEY: unsure
<222> LOCATION: (97)
<223> OTHER INFORMATION: Xaa = unknown
<220> FEATURE:
<221> NAME/KEY: unsure
<222> LOCATION: (108)
<223> OTHER INFORMATION: Xaa = unknown
<220> FEATURE:
<221> NAME/KEY: unsure
<222> LOCATION: (191)
<223> OTHER INFORMATION: Xaa = unknown
<220> FEATURE:
<221> NAME/KEY: unsure
<222> LOCATION: (203)
<223> OTHER INFORMATION: Xaa = unknown
<220> FEATURE:
<221> NAME/KEY: unsure
<222> LOCATION: (225)
```

<223> OTHER INFORMATION: Xaa = unknown
<220> FEATURE:
<221> NAME/KEY: unsure
<222> LOCATION: (230)
<223> OTHER INFORMATION: Xaa = unknown
<220> FEATURE:
<221> NAME/KEY: unsure
<222> LOCATION: (232)
<223> OTHER INFORMATION: Xaa = unknown

<400> SEQUENCE: 1

```
c  ggt ncc ant ncc ccn anc ccg gta ntt aac cgg att ccc ana ntg ccc      49
   Gly Xaa Xaa Xaa Pro Xaa Pro Val Xaa Asn Arg Ile Pro Xaa Xaa Pro
    1               5                  10                  15 caa aan gng ccc ncc ccn gaa taa     aat tcc tna ann cnc nng ntg gcc      97
Gln Xaa Xaa Pro Xaa Pro Glu         Asn Ser Xaa Xaa Xaa Xaa Xaa Ala
                 20                  25                  30 can tta cca acc cnn gaa acc nan aaa tnt ggg gnn cct nag ggn ccc         145
Xaa Leu Pro Thr Xaa Glu Thr Xaa Lys Xaa Gly Xaa Pro Xaa Xaa Pro
                 35                  40                  45 cag aac tna cac caa naa att ttn aan cca ana aac nna ngg ccc cct         193
Gln Asn Xaa His Gln Xaa Ile Xaa Xaa Pro Xaa Asn Xaa Xaa Pro Pro
 50                  55                  60 ttt gaa ccc act cat ggg cgc cta act taa     ggt ggc cgc cct gtt ccg     241
Phe Glu Pro Thr His Gly Arg Leu Thr         Gly Gly Arg Pro Val Pro
 65                  70                  75                  80 ngg tcg aat gtc cca tga aan aag tgg acg aac aga tgc tga atg tgc         289
Xaa Ser Asn Val Pro     Xaa Lys Trp Thr Asn Arg Cys     Met Cys
                 85                      90                  95 agn aac aaa gaa ttc caa gct act ttg tcg aat ggn atc ccg aat aac         337
Xaa Asn Lys Glu Phe Gln Ala Thr Leu Ser Asn Xaa Ile Pro Asn Asn
                100                 105                 110 gtg aaa act gcg gtt tgt gac att cca cct agg ggc ctt aaa atg tcg         385
Val Lys Thr Ala Val Cys Asp Ile Pro Pro Arg Gly Leu Lys Met Ser
                115                 120                 125 gtc aca ttt gtt ggc aat agt act gcc ata caa gaa cta ttc aaa cgt         433
Val Thr Phe Val Gly Asn Ser Thr Ala Ile Gln Glu Leu Phe Lys Arg
                130                 135                 140 gtc tcc gag cag ttc acc gca atg ttc cgt cgc aaa gca ttc ttg cat         481
Val Ser Glu Gln Phe Thr Ala Met Phe Arg Arg Lys Ala Phe Leu His
145                 150                 155                 160 tgg tac aca ggc gaa ggt atg gac gag atg gag ttc acc gag gcc gaa         529
Trp Tyr Thr Gly Glu Gly Met Asp Glu Met Glu Phe Thr Glu Ala Glu
                165                 170                 175 tcg aac atg aac gat ctg gtc agt gaa tat cag caa tac caa gan gca         577
Ser Asn Met Asn Asp Leu Val Ser Glu Tyr Gln Gln Tyr Gln Xaa Ala
                180                 185                 190 acc gct gag gag gaa ggc gaa ttc cag ctg anc gcc ggc gct acc att         625
Thr Ala Glu Glu Glu Gly Glu Phe Gln Leu Xaa Ala Gly Ala Thr Ile
                195                 200                 205 acc agt tgg tct ggt gtc aaa tcc cag cat ggc gcc gga gca tcg acg         673
Thr Ser Trp Ser Gly Val Lys Ser Gln His Gly Ala Gly Ala Ser Thr
                210                 215                 220 nng ccc aat cgc cct nng tag cgn tta                                     700
Xaa Pro Asn Arg Pro Xaa     Xaa Leu
225                 230
```

<210> SEQ ID NO 2
<211> LENGTH: 23
<212> TYPE: PRT
<213> ORGANISM: Fasciola hepatica
<220> FEATURE:
<221> NAME/KEY: unsure

```
<222> LOCATION: (2)..(4)
<223> OTHER INFORMATION: Xaa = unknown
<220> FEATURE:
<221> NAME/KEY: unsure
<222> LOCATION: (6)
<223> OTHER INFORMATION: Xaa = unknown
<220> FEATURE:
<221> NAME/KEY: unsure
<222> LOCATION: (9)
<223> OTHER INFORMATION: Xaa = unknown
<220> FEATURE:
<221> NAME/KEY: unsure
<222> LOCATION: (14)..(15)
<223> OTHER INFORMATION: Xaa = unknown
<220> FEATURE:
<221> NAME/KEY: unsure
<222> LOCATION: (18)..(19)
<223> OTHER INFORMATION: Xaa = unknown
<220> FEATURE:
<221> NAME/KEY: unsure
<222> LOCATION: (21)
<223> OTHER INFORMATION: Xaa = unknown

<400> SEQUENCE: 2

Gly Xaa Xaa Xaa Pro Xaa Pro Val Xaa Asn Arg Ile Pro Xaa Xaa Pro
 1               5                  10                  15

Gln Xaa Xaa Pro Xaa Pro Glu
            20

<210> SEQ ID NO 3
<211> LENGTH: 49
<212> TYPE: PRT
<213> ORGANISM: Fasciola hepatica
<220> FEATURE:
<221> NAME/KEY: unsure
<222> LOCATION: (3)..(7)
<223> OTHER INFORMATION: Xaa = unknown
<220> FEATURE:
<221> NAME/KEY: unsure
<222> LOCATION: (9)
<223> OTHER INFORMATION: Xaa = unknown
<220> FEATURE:
<221> NAME/KEY: unsure
<222> LOCATION: (13)
<223> OTHER INFORMATION: Xaa = unknown
<220> FEATURE:
<221> NAME/KEY: unsure
<222> LOCATION: (16)
<223> OTHER INFORMATION: Xaa = unknown
<220> FEATURE:
<221> NAME/KEY: unsure
<222> LOCATION: (18)
<223> OTHER INFORMATION: Xaa = unknown
<220> FEATURE:
<221> NAME/KEY: unsure
<222> LOCATION: (20)
<223> OTHER INFORMATION: Xaa = unknown
<220> FEATURE:
<221> NAME/KEY: unsure
<222> LOCATION: (22)..(23)
<223> OTHER INFORMATION: Xaa = unknown
<220> FEATURE:
<221> NAME/KEY: unsure
<222> LOCATION: (27)
<223> OTHER INFORMATION: Xaa = unknown
<220> FEATURE:
<221> NAME/KEY: unsure
<222> LOCATION: (30)
<223> OTHER INFORMATION: Xaa = unknown
<220> FEATURE:
<221> NAME/KEY: unsure
<222> LOCATION: (32)..(33)
<223> OTHER INFORMATION: Xaa = unknown
<220> FEATURE:
<221> NAME/KEY: unsure
<222> LOCATION: (35)
```

```
<223> OTHER INFORMATION: Xaa = unknown
<220> FEATURE:
<221> NAME/KEY: unsure
<222> LOCATION: (37)..(38)
<223> OTHER INFORMATION: Xaa = unknown

<400> SEQUENCE: 3

Asn Ser Xaa Xaa Xaa Xaa Xaa Ala Xaa Leu Pro Thr Xaa Glu Thr Xaa
 1               5                  10                  15

Lys Xaa Gly Xaa Pro Xaa Xaa Pro Gln Asn Xaa His Gln Xaa Ile Xaa
            20                  25                  30

Xaa Pro Xaa Asn Xaa Xaa Pro Pro Phe Glu Pro Thr His Gly Arg Leu
        35                  40                  45

Thr

<210> SEQ ID NO 4
<211> LENGTH: 11
<212> TYPE: PRT
<213> ORGANISM: Fasciola hepatica
<220> FEATURE:
<221> NAME/KEY: unsure
<222> LOCATION: (7)
<223> OTHER INFORMATION: Xaa = unknown

<400> SEQUENCE: 4

Gly Gly Arg Pro Val Pro Xaa Ser Asn Val Pro
 1               5                  10

<210> SEQ ID NO 5
<211> LENGTH: 7
<212> TYPE: PRT
<213> ORGANISM: Fasciola hepatica
<220> FEATURE:
<221> NAME/KEY: unsure
<222> LOCATION: (1)
<223> OTHER INFORMATION: Xaa = unknown

<400> SEQUENCE: 5

Xaa Lys Trp Thr Asn Arg Cys
 1               5

<210> SEQ ID NO 6
<211> LENGTH: 136
<212> TYPE: PRT
<213> ORGANISM: Fasciola hepatica
<220> FEATURE:
<221> NAME/KEY: unsure
<222> LOCATION: (3)
<223> OTHER INFORMATION: Xaa = unknown
<220> FEATURE:
<221> NAME/KEY: unsure
<222> LOCATION: (14)
<223> OTHER INFORMATION: Xaa = unknown
<220> FEATURE:
<221> NAME/KEY: unsure
<222> LOCATION: (97)
<223> OTHER INFORMATION: Xaa = unknown
<220> FEATURE:
<221> NAME/KEY: unsure
<222> LOCATION: (109)
<223> OTHER INFORMATION: Xaa = unknown
<220> FEATURE:
<221> NAME/KEY: unsure
<222> LOCATION: (131)
<223> OTHER INFORMATION: Xaa = unknown
<220> FEATURE:
<221> NAME/KEY: unsure
<222> LOCATION: (136)
<223> OTHER INFORMATION: Xaa = unknown
```

-continued

```
<400> SEQUENCE: 6

Met Cys Xaa Asn Lys Glu Phe Gln Ala Thr Leu Ser Asn Xaa Ile Pro
 1               5                  10                  15

Asn Asn Val Lys Thr Ala Val Cys Asp Ile Pro Pro Arg Gly Leu Lys
             20                  25                  30

Met Ser Val Thr Phe Val Gly Asn Ser Thr Ala Ile Gln Glu Leu Phe
         35                  40                  45

Lys Arg Val Ser Glu Gln Phe Thr Ala Met Phe Arg Arg Lys Ala Phe
     50                  55                  60

Leu His Trp Tyr Thr Gly Glu Gly Met Asp Glu Met Glu Phe Thr Glu
 65                  70                  75                  80

Ala Glu Ser Asn Met Asn Asp Leu Val Ser Glu Tyr Gln Gln Tyr Gln
                 85                  90                  95

Xaa Ala Thr Ala Glu Glu Glu Gly Glu Phe Gln Leu Xaa Ala Gly Ala
            100                 105                 110

Thr Ile Thr Ser Trp Ser Gly Val Lys Ser Gln His Gly Ala Gly Ala
        115                 120                 125

Ser Thr Xaa Pro Asn Arg Pro Xaa
    130                 135

<210> SEQ ID NO 7
<211> LENGTH: 141
<212> TYPE: PRT
<213> ORGANISM: Fasciola hepatica

<400> SEQUENCE: 7

Arg Cys Met Cys Glx Asn Lys Glu Phe Gln Ala Thr Leu Ser Asn Glx
 1               5                  10                  15

Ile Pro Asn Asn Val Lys Thr Ala Val Cys Asp Ile Pro Pro Arg Gly
             20                  25                  30

Leu Lys Met Ser Val Thr Phe Val Gly Asn Ser Thr Ala Ile Gln Glu
         35                  40                  45

Leu Phe Lys Arg Val Ser Glu Gln Phe Thr Ala Met Phe Arg Arg Lys
     50                  55                  60

Ala Phe Leu His Trp Tyr Thr Gly Glu Gly Met Asp Glu Met Glu Phe
 65                  70                  75                  80

Thr Glu Ala Glu Ser Asn Met Asn Asp Leu Val Ser Glu Tyr Gln Gln
                 85                  90                  95

Tyr Gln Glx Ala Thr Ala Glu Glu Glu Gly Glu Phe Gln Leu Glx Ala
            100                 105                 110

Gly Ala Thr Ile Thr Ser Trp Ser Gly Val Lys Ser Gln His Gly Ala
        115                 120                 125

Gly Ala Ser Thr Glx Pro Asn Arg Pro Glx Asx Glx Leu
    130                 135                 140

<210> SEQ ID NO 8
<211> LENGTH: 449
<212> TYPE: PRT
<213> ORGANISM: Toxoplasma gondii
<300> PUBLICATION INFORMATION:
<301> AUTHORS: Nagel, S. D.
       Boothroyd, J. C.
<302> TITLE: The a and b tubulins of Taxoplasma gondii are encoded
       by single copy genes containing multiple copy introns.
<303> JOURNAL: Mol. Biochem. Parasitol.
<304> VOLUME: 29
<306> PAGES: 261-273
<307> DATE: 1988
<300> PUBLICATION INFORMATION:
```

-continued

<302> TITLE: GenBank Acession no. P10878

<400> SEQUENCE: 8

```
Met Arg Glu Ile Val His Val Gln Gly Gln Cys Gly Asn Gln Ile
 1               5                  10                  15

Gly Ala Lys Phe Trp Glu Val Ile Ser Asp Glu His Gly Ile Asp Pro
                20                  25                  30

Thr Gly Thr Tyr Cys Gly Asp Ser Asp Leu Gln Leu Glu Arg Ile Asn
            35                  40                  45

Val Phe Tyr Asn Glu Ala Thr Gly Gly Arg Phe Val Pro Arg Ala Ile
    50                  55                  60

Leu Met Asp Leu Glu Pro Gly Thr Met Asp Ser Val Arg Ala Gly Pro
 65                  70                  75                  80

Phe Gly Gln Leu Phe Arg Pro Asp Asn Phe Val Phe Gly Gln Thr Gly
                85                  90                  95

Ala Gly Asn Asn Trp Ala Lys Gly His Tyr Thr Glu Gly Ala Glu Leu
            100                 105                 110

Ile Asp Ser Val Leu Asp Val Val Arg Lys Glu Ala Glu Gly Cys Asp
        115                 120                 125

Cys Leu Gln Gly Phe Gln Ile Thr His Ser Leu Gly Gly Gly Thr Gly
    130                 135                 140

Ser Gly Met Gly Thr Leu Leu Ile Ser Lys Val Arg Glu Glu Tyr Pro
145                 150                 155                 160

Asp Arg Ile Met Glu Thr Phe Ser Val Phe Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Ala Asp Glu Val Gln Val Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Ala Met Ser Gly Val Thr Cys Cys Leu
225                 230                 235                 240

Arg Phe Pro Gly Gln Leu Asn Ser Asp Leu Arg Lys Leu Ala Val Asn
                245                 250                 255

Leu Val Pro Phe Pro Arg Leu His Phe Phe Leu Ile Gly Phe Ala Pro
            260                 265                 270

Leu Thr Ser Arg Gly Ser Gln Gln Tyr Arg Ala Leu Ser Val Pro Glu
        275                 280                 285

Leu Thr Gln Gln Met Phe Asp Ala Lys Asn Met Met Cys Ala Ser Asp
    290                 295                 300

Pro Arg His Gly Arg Tyr Leu Thr Ala Ser Ala Met Phe Arg Gly Arg
305                 310                 315                 320

Met Ser Thr Lys Glu Val Asp Glu Gln Met Leu Asn Val Gln Asn Lys
                325                 330                 335

Asn Ser Ser Tyr Phe Val Glu Trp Ile Pro Asn Asn Met Lys Ser Ser
            340                 345                 350

Val Cys Asp Ile Pro Pro Lys Gly Leu Lys Met Ser Val Thr Phe Val
        355                 360                 365

Gly Asn Ser Thr Ala Ile Gln Glu Met Phe Lys Arg Val Ser Asp Gln
    370                 375                 380

Phe Thr Ala Met Phe Arg Arg Lys Ala Phe Leu His Trp Tyr Thr Gly
385                 390                 395                 400
```

```
Glu Gly Met Asp Glu Met Glu Phe Thr Glu Ala Glu Ser Asn Met Asn
            405                 410                 415

Asp Leu Val Ser Glu Tyr Gln Gln Tyr Gln Asp Ala Thr Ala Glu Glu
            420                 425                 430

Glu Gly Glu Phe Asp Glu Glu Gly Glu Met Gly Ala Glu Glu Gly
            435                 440                 445

Ala

<210> SEQ ID NO 9
<211> LENGTH: 1163
<212> TYPE: DNA
<213> ORGANISM: Fasciola hepatica
<220> FEATURE:
<221> NAME/KEY: CDS
<222> LOCATION: (179)..(763)
<220> FEATURE:
<221> NAME/KEY: unsure
<222> LOCATION: (90)
<223> OTHER INFORMATION: n = a or t or c or g
<220> FEATURE:
<221> NAME/KEY: unsure
<222> LOCATION: (856)
<223> OTHER INFORMATION: n = a or t or c or g
<220> FEATURE:
<221> NAME/KEY: unsure
<222> LOCATION: (955)
<223> OTHER INFORMATION: n = a or t or c or g
<220> FEATURE:
<221> NAME/KEY: unsure
<222> LOCATION: (1026)
<223> OTHER INFORMATION: n = a or t or c or g
<220> FEATURE:
<221> NAME/KEY: unsure
<222> LOCATION: (1043)
<223> OTHER INFORMATION: n = a or t or c or g
<220> FEATURE:
<221> NAME/KEY: unsure
<222> LOCATION: (1046)
<223> OTHER INFORMATION: n = a or t or c or g
<220> FEATURE:
<221> NAME/KEY: unsure
<222> LOCATION: (1050)
<223> OTHER INFORMATION: n = a or t or c or g
<220> FEATURE:
<221> NAME/KEY: unsure
<222> LOCATION: (1053)
<223> OTHER INFORMATION: n = a or t or c or g
<220> FEATURE:
<221> NAME/KEY: unsure
<222> LOCATION: (1056)
<223> OTHER INFORMATION: n = a or t or c or g
<220> FEATURE:
<221> NAME/KEY: unsure
<222> LOCATION: (1122)
<223> OTHER INFORMATION: n = a or t or c or g

<400> SEQUENCE: 9
tcgctcacta tagggcgaat tgggcccgac gtcgcatgcc cccggccgcc atggccgcgg      60
gattggtggc gacgactcct ggagcccgtn agtatcagcg gaattccggt gtgatcgcaa     120
tcagtgctct ccgggcgcc atccacttcc ccactctcat ccgcatttcc aaagaccg        178 atg ttg cag cct aat atg ccc gcc ccg aat ttt tct gga cag gcg gta      226
Met Leu Gln Pro Asn Met Pro Ala Pro Asn Phe Ser Gly Gln Ala Val
  1               5                  10                  15 gtg ggc aag gag ttc gaa acc atc agt tta tca gac tac aag ggc aaa      274
Val Gly Lys Glu Phe Glu Thr Ile Ser Leu Ser Asp Tyr Lys Gly Lys
             20                  25                  30 tgg gtg att ctc gcc ttc tat cca ctt gat ttc acg ttc gtg tgt cca      322
Trp Val Ile Leu Ala Phe Tyr Pro Leu Asp Phe Thr Phe Val Cys Pro
         35                  40                  45
```

| | | | | | | | | | | | | | | | |
|---|---|---|---|---|---|---|---|---|---|---|---|---|---|---|---|
| acg | gaa | ata | atc | gcg | atc | agt | gat | cag | atg | gag | cag | ttc | gca | caa | cgt | 370 |
| Thr | Glu | Ile | Ile | Ala | Ile | Ser | Asp | Gln | Met | Glu | Gln | Phe | Ala | Gln | Arg | |
| | 50 | | | | | 55 | | | | | 60 | | | | | |
| aac | tgc | gcc | gtc | atc | ttc | tgc | tct | act | gac | tcg | gtt | tat | tcg | cat | ctg | 418 |
| Asn | Cys | Ala | Val | Ile | Phe | Cys | Ser | Thr | Asp | Ser | Val | Tyr | Ser | His | Leu | |
| 65 | | | | | 70 | | | | | 75 | | | | | 80 | |
| caa | tgg | acc | aaa | atg | gat | cgt | aag | gtt | ggc | ggt | ata | ggc | cag | ctg | aac | 466 |
| Gln | Trp | Thr | Lys | Met | Asp | Arg | Lys | Val | Gly | Gly | Ile | Gly | Gln | Leu | Asn | |
| | | | | 85 | | | | | 90 | | | | | 95 | | |
| ttc | ccg | ctg | ctg | gca | gac | aag | aat | atg | tct | gtc | tct | cgc | gcc | ttt | ggt | 514 |
| Phe | Pro | Leu | Leu | Ala | Asp | Lys | Asn | Met | Ser | Val | Ser | Arg | Ala | Phe | Gly | |
| | | | 100 | | | | | 105 | | | | | 110 | | | |
| gtt | ctg | gat | gag | gaa | cag | ggt | aat | acc | tac | cgt | ggc | aat | ttc | ctc | atc | 562 |
| Val | Leu | Asp | Glu | Glu | Gln | Gly | Asn | Thr | Tyr | Arg | Gly | Asn | Phe | Leu | Ile | |
| | | 115 | | | | | 120 | | | | | 125 | | | | |
| gat | ccc | aag | ggg | gtc | ctg | cgc | cag | atc | acg | gtg | aat | gac | gac | ccg | gtg | 610 |
| Asp | Pro | Lys | Gly | Val | Leu | Arg | Gln | Ile | Thr | Val | Asn | Asp | Asp | Pro | Val | |
| | 130 | | | | | 135 | | | | | 140 | | | | | |
| ggc | cgt | tcc | gtt | gaa | gaa | gcc | ttg | cgt | ctg | ctc | gat | gca | ttc | ata | ttc | 658 |
| Gly | Arg | Ser | Val | Glu | Glu | Ala | Leu | Arg | Leu | Leu | Asp | Ala | Phe | Ile | Phe | |
| 145 | | | | | 150 | | | | | 155 | | | | | 160 | |
| cac | gag | gag | cat | gga | gag | gtc | tgc | ccg | gcg | aac | tgg | aag | cct | aaa | agc | 706 |
| His | Glu | Glu | His | Gly | Glu | Val | Cys | Pro | Ala | Asn | Trp | Lys | Pro | Lys | Ser | |
| | | | | 165 | | | | | 170 | | | | | 175 | | |
| aag | acc | atc | gtg | cct | act | ccg | gat | gga | tcc | aaa | gca | tat | ttc | tcc | tca | 754 |
| Lys | Thr | Ile | Val | Pro | Thr | Pro | Asp | Gly | Ser | Lys | Ala | Tyr | Phe | Ser | Ser | |
| | | | 180 | | | | | 185 | | | | | 190 | | | |

| | | | | |
|---|---|---|---|---|
| gcc aac tag tgaacaaggg tgcttaatcc cggctctgtg tttcgtttct | | | | | 803 |
| Ala Asn | | | | | |
| 195 | | | | | | ggtttaaaat aaattagata atacggtgca aaaaaaaaa aaaaaacgga atnccggtac 863 ggtaacagtt cccaagcgca acagtatgat gagaatccaa ctgattatcg tcttggaatc 923 gctcattggt ttcgcaacca gttttcgact gnaggcaacc gcattcaagg attgtgctc 983 gcaacttgcc gaattgatga atgtgactgt gaaaccatgt gnactactc tgtgtagtgn 1043 gtntcgnggn ganaacgccc aactggaaat cacttcccga acaaaggaag ttggcaagtc 1103 ttgaaagcag tcggccgtnc aatagtcgga cgtgtttctg cccatccccc tggatgacta 1163

<210> SEQ ID NO 10
<211> LENGTH: 194
<212> TYPE: PRT
<213> ORGANISM: Fasciola hepatica

<400> SEQUENCE: 10

| | | | | | | | | | | | | | | |
|---|---|---|---|---|---|---|---|---|---|---|---|---|---|---|
| Met | Leu | Gln | Pro | Asn | Met | Pro | Ala | Pro | Asn | Phe | Ser | Gly | Gln | Ala | Val |
| 1 | | | | 5 | | | | | 10 | | | | | 15 | |

| | | | | | | | | | | | | | | |
|---|---|---|---|---|---|---|---|---|---|---|---|---|---|---|
| Val | Gly | Lys | Glu | Phe | Glu | Thr | Ile | Ser | Leu | Ser | Asp | Tyr | Lys | Gly | Lys |
| | | | 20 | | | | | 25 | | | | | 30 | | |

| | | | | | | | | | | | | | | |
|---|---|---|---|---|---|---|---|---|---|---|---|---|---|---|
| Trp | Val | Ile | Leu | Ala | Phe | Tyr | Pro | Leu | Asp | Phe | Thr | Phe | Val | Cys | Pro |
| | | 35 | | | | | 40 | | | | | 45 | | | |

| | | | | | | | | | | | | | | |
|---|---|---|---|---|---|---|---|---|---|---|---|---|---|---|
| Thr | Glu | Ile | Ile | Ala | Ile | Ser | Asp | Gln | Met | Glu | Gln | Phe | Ala | Gln | Arg |
| | 50 | | | | | 55 | | | | | 60 | | | | |

| | | | | | | | | | | | | | | |
|---|---|---|---|---|---|---|---|---|---|---|---|---|---|---|
| Asn | Cys | Ala | Val | Ile | Phe | Cys | Ser | Thr | Asp | Ser | Val | Tyr | Ser | His | Leu |
| 65 | | | | | 70 | | | | | 75 | | | | | 80 |

| | | | | | | | | | | | | | | |
|---|---|---|---|---|---|---|---|---|---|---|---|---|---|---|
| Gln | Trp | Thr | Lys | Met | Asp | Arg | Lys | Val | Gly | Gly | Ile | Gly | Gln | Leu | Asn |
| | | | | 85 | | | | | 90 | | | | | 95 | |

```
Phe Pro Leu Leu Ala Asp Lys Asn Met Ser Val Ser Arg Ala Phe Gly
            100                 105                 110

Val Leu Asp Glu Glu Gln Gly Asn Thr Tyr Arg Gly Asn Phe Leu Ile
        115                 120                 125

Asp Pro Lys Gly Val Leu Arg Gln Ile Thr Val Asn Asp Asp Pro Val
    130                 135                 140

Gly Arg Ser Val Glu Glu Ala Leu Arg Leu Leu Asp Ala Phe Ile Phe
145                 150                 155                 160

His Glu Glu His Gly Glu Val Cys Pro Ala Asn Trp Lys Pro Lys Ser
                165                 170                 175

Lys Thr Ile Val Pro Thr Pro Asp Gly Ser Lys Ala Tyr Phe Ser Ser
                180                 185                 190

Ala Asn
```

<210> SEQ ID NO 11
<211> LENGTH: 198
<212> TYPE: PRT
<213> ORGANISM: Rattus rattus
<300> PUBLICATION INFORMATION:
<302> TITLE: GenBank accession no. P35704

<400> SEQUENCE: 11

```
Met Ala Ser Gly Asn Ala His Ile Gly Lys Pro Ala Pro Asp Phe Thr
1               5                   10                  15

Gly Thr Ala Val Val Asp Gly Ala Phe Lys Glu Ile Lys Leu Ser Asp
            20                  25                  30

Tyr Arg Gly Lys Tyr Val Val Leu Phe Phe Tyr Pro Leu Asp Phe Thr
        35                  40                  45

Phe Val Cys Pro Thr Glu Ile Ile Ala Phe Ser Asp His Ala Glu Asp
    50                  55                  60

Phe Arg Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Lys Ser Leu Ser
            100                 105                 110

Gln Asn Tyr Gly Val Leu Lys Asn Asp Glu Gly Ile Ala Tyr Arg Gly
        115                 120                 125

Leu Phe Ile Ile Asp Ala Lys Gly Val Leu Arg Gln Ile Thr Val Asn
    130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
                180                 185                 190

Tyr Phe Ser Lys His Asn
        195
```

<210> SEQ ID NO 12
<211> LENGTH: 198
<212> TYPE: PRT
<213> ORGANISM: Homo sapiens
<300> PUBLICATION INFORMATION:
<302> TITLE: GenBank accession no. P31945

<400> SEQUENCE: 12

```
Met Ala Ser Gly Asn Ala Arg Ile Gly Lys Pro Ala Pro Asp Phe Lys
1               5                   10                  15

Ala Thr Ala Val Val Asp Gly Ala Phe Lys Glu Val Lys Leu Ser Asp
            20                  25                  30

Tyr Lys Gly Lys Tyr Val Val Leu Phe Phe Tyr Pro Leu Asp Phe Thr
                35                  40                  45

Phe Val Cys Pro Thr Glu Ile Ile Ala Phe Ser Asn Arg Ala Glu Asp
        50                  55                  60

Phe Arg Lys Leu Glu Val Leu Gly Val Ser Val Asp Ser Gln Phe Asn
65                  70                  75                  80

His Leu Ala Trp Ile Asn Thr Pro Arg Lys Glu Gly Gly Leu Gly Pro
                85                  90                  95

Leu Asn Ile Pro Leu Leu Gly Asp Val Thr Arg Arg Leu Ser Glu Asp
            100                 105                 110

Tyr Gly Val Leu Lys Thr Asp Glu Gly Ile Ala Tyr Arg Gly Leu Phe
                115                 120                 125

Ile Ile Asp Gly Lys Gly Val Leu Arg Gln Ile Thr Val Asn Asp Leu
130                 135                 140

Pro Val Gly Arg Ser Val Asp Glu Ala Leu Arg Leu Val Gln Ala Phe
145                 150                 155                 160

Gln Tyr Thr Asp Glu His Gly Glu Val Cys Pro Ala Gly Trp Lys Pro
                165                 170                 175

Gly Ser Asp Thr Ile Lys Pro Asn Val Asp Asp Ser Lys Glu Tyr Phe
            180                 185                 190

Ser Lys His Asn Asn Glu
            195

<210> SEQ ID NO 13
<211> LENGTH: 198
<212> TYPE: PRT
<213> ORGANISM: Homo sapiens
<300> PUBLICATION INFORMATION:
<302> TITLE: GenBank accession no. X67951

<400> SEQUENCE: 13

Met Ser Ser Gly Asn Ala Lys Ile Gly His Pro Ala Pro Asn Phe Lys
1               5                   10                  15

Ala Thr Ala Val Met Pro Asp Gly Phe Lys Asp Ile Ser Leu Ser Asp
            20                  25                  30

Tyr Lys Gly Lys Tyr Val Val Phe Phe Tyr Pro Leu Asp Phe Thr
                35                  40                  45

Phe Val Cys Pro Thr Glu Ile Ile Ala Phe Ser Asp Arg Ala Glu Glu
        50                  55                  60

Phe Lys Lys Leu Asn Cys Gln Val Ile Gly Ala Ser Val Asp Ser His
65                  70                  75                  80

Phe Cys His Leu Ala Trp Val Asn Thr Pro Lys Lys Gln Gly Gly Leu
                85                  90                  95

Gly Pro Met Asn Ile Pro Leu Val Ser Asp Pro Lys Arg Thr Ile Ala
            100                 105                 110

Gln Asp Tyr Gly Val Leu Lys Ala Asp Glu Gly Ile Ser Phe Arg Gly
                115                 120                 125

Leu Phe Ile Ile Asp Asp Lys Gly Ile Leu Arg Gln Ile Thr Val Asn
130                 135                 140

Asp Leu Pro Val Gly Arg Ser Val Asp Glu Thr Leu Arg Leu Val Gln
145                 150                 155                 160
```

```
Ala Phe Gln Phe Thr Asp Lys His Gly Glu Val Cys Pro Ala Gly Trp
                165                 170                 175

Lys Pro Gly Ser Asp Thr Ile Lys Pro Asp Val Gln Lys Ser Lys Glu
            180                 185                 190

Tyr Phe Ser Lys Gln Lys
            195

<210> SEQ ID NO 14
<211> LENGTH: 198
<212> TYPE: PRT
<213> ORGANISM: Homo sapiens
<300> PUBLICATION INFORMATION:
<301> AUTHORS: Lim, Y. S.
      Cha, M. K.
      Kim, H. K.
<302> TITLE: The thiol-specific antioxidant protein from human
      brain: gene cloning and analysis of conserved cysteine
      regions.
<303> JOURNAL: Gene
<304> VOLUME: 140
<306> PAGES: 279-284
<307> DATE: 1994
<300> PUBLICATION INFORMATION:
<302> TITLE: GenBank accession no. P35701

<400> SEQUENCE: 14

Met Ala Ser Gly Asn Ala Arg Ile Gly Lys Pro Ala Pro Asp Phe Lys
 1               5                  10                  15

Ala Thr Ala Val Val Asp Gly Ala Phe Lys Glu Val Lys Leu Ser Asp
                20                  25                  30

Tyr Lys Gly Lys Tyr Val Val Leu Phe Phe Tyr Pro Leu Asp Phe Thr
            35                  40                  45

Phe Val Cys Pro Thr Glu Ile Ile Ala Phe Thr Thr Val Lys Arg Thr
    50                  55                  60

Ser Ala Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Arg Arg Leu Ser
            100                 105                 110

Glu Asp Tyr Gly Val Leu Lys Asn Asp Glu Gly Ile Ala Tyr Arg Gly
        115                 120                 125

Leu Phe Ile Ile Asp Gly Lys Gly Val Leu Arg Gln Ile Thr Val Asn
130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Ala Trp
                165                 170                 175

Lys Pro Gly Arg Asp Thr Ile Lys Pro Asn Val Asp Asp Ser Lys Glu
            180                 185                 190

Tyr Phe Ser Lys His Asn
            195

<210> SEQ ID NO 15
<211> LENGTH: 161
<212> TYPE: PRT
<213> ORGANISM: Onchocerca volvulus
<300> PUBLICATION INFORMATION:
<302> TITLE: GenBank accession no. U09385

<400> SEQUENCE: 15
```

```
Glu Phe Lys Lys Arg Asn Val Lys Leu Ile Gly Leu Ser Cys Asp Ser
  1               5                  10                  15

Ala Asp Ser His Ser Lys Trp Ala Asp Ile Leu Ala Leu Tyr Lys
             20                  25                  30

Met Lys Cys Val Gly Cys Asp Ser Glu Lys Lys Leu Pro Tyr Pro Ile
         35                  40                  45

Ile Ala Asp Glu Asp Arg Ser Leu Ala Thr Glu Leu Gly Met Met Asp
     50                  55                  60

Pro Asp Glu Arg Asp Glu Lys Gly Asn Thr Leu Thr Ala Arg Cys Val
 65                  70                  75                  80

Phe Ile Ile Gly Ser Asp Lys Thr Leu Lys Leu Ser Ile Leu Tyr Pro
             85                  90                  95

Ala Thr Thr Gly Arg Asn Phe Asp Glu Ile Leu Arg Val Val Asp Ser
            100                 105                 110

Leu Gln Leu Thr Ala Val Lys Leu Val Ala Thr Pro Val Asp Trp Lys
            115                 120                 125

Asp Gly Asp Asp Cys Val Val Leu Pro Thr Ile Asp Asp Asn Glu Ala
            130                 135                 140

Lys Lys Leu Phe Gly Glu Lys Ile His Thr Ile Asp Leu Pro Ser Gly
145                 150                 155                 160

Lys
```

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Primer
      coding for the conserved active site region, Cys 47.
<220> FEATURE:
<221> NAME/KEY: misc_structure
<222> LOCATION: (6)
<223> OTHER INFORMATION: y = t or c
<220> FEATURE:
<221> NAME/KEY: misc_structure
<222> LOCATION: (9)
<223> OTHER INFORMATION: r = a or g
<220> FEATURE:
<221> NAME/KEY: misc_structure
<222> LOCATION: (21)
<223> OTHER INFORMATION: r = a or g
<220> FEATURE:
<221> NAME/KEY: misc_structure
<222> LOCATION: (24)
<223> OTHER INFORMATION: r = a or g
<220> FEATURE:
<221> NAME/KEY: misc_structure
<222> LOCATION: (15)
<223> OTHER INFORMATION: n = a or g or t or c
<220> FEATURE:
<221> NAME/KEY: misc_structure
<222> LOCATION: (12)
<223> OTHER INFORMATION: y = t or c

<400> SEQUENCE: 16
gatttyacrt tygtntgtcc racrga                                    26

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer
      coding for the conserved active site region, Cys 168
<220> FEATURE:
<221> NAME/KEY: misc_structure

```
<222> LOCATION: (3)
<223> OTHER INFORMATION: w = a or g
<220> FEATURE:
<221> NAME/KEY: misc_structure
<222> LOCATION: (9)
<223> OTHER INFORMATION: y = t or c
<220> FEATURE:
<221> NAME/KEY: misc_structure
<222> LOCATION: (12)
<223> OTHER INFORMATION: w = a or g
<220> FEATURE:
<221> NAME/KEY: misc_structure
<222> LOCATION: (18)
<223> OTHER INFORMATION: y = t or c
<220> FEATURE:
<221> NAME/KEY: misc_structure
<222> LOCATION: (6)
<223> OTHER INFORMATION: n = a or g or t or c

<400> SEQUENCE: 17
ggwcanacyt cwccatgytc                                            20

<210> SEQ ID NO 18
<211> LENGTH: 8
<212> TYPE: DNA
<213> ORGANISM: Fasciola hepatica

<400> SEQUENCE: 18 aaaataaa                                                          8

<210> SEQ ID NO 19
<211> LENGTH: 4
<212> TYPE: DNA
<213> ORGANISM: Fasciola hepatica

<400> SEQUENCE: 19 aata                                                              4

<210> SEQ ID NO 20
<211> LENGTH: 16
<212> TYPE: PRT
<213> ORGANISM: Fasciola hepatica

<400> SEQUENCE: 20

Phe Tyr Pro Leu Asp Phe Thr Phe Val Cys Pro Thr Glu Ile Ile Ala
 1               5                  10                  15

<210> SEQ ID NO 21
<211> LENGTH: 7
<212> TYPE: PRT
<213> ORGANISM: Fasciola hepatica

<400> SEQUENCE: 21

His Gly Glu Val Cys Pro Ala
 1               5
```

VACCINE CONTAINING A PEROXIREDOXIN AND/OR A β-TUBULIN

The invention relates to the use of a peroxiredoxin (thiol-specific antioxidant) and/or a β-tubulin as a protective antigen against helminth parasites.

Each species of domestic animal can be parasitised by a number of different species of helminth, a process which usually causes disease. For example, the parasitic trematode *Fasciola hepatica* is known to be one cause of the economically important disease fascioliasis in ruminants, such as cattle and sheep. The parasite enters the mammalian host by penetrating the gut wall and spends approximately seven weeks feeding on and burrowing through the liver mass before migrating into the bile duct. Following infection, development of immunity in the host can be poor and resistance to reinfection in already infected hosts may be only partial or non-existent. Other parasitic flukes include *Fasciola gigantica* and Dicrocoelium spp., Paramphistomum spp. and also Schistosoma spp., eg *S. bovis* and *S. mansoni*.

Problems are also caused by nematodes such as hookworms (e.g. Necator, Ancylostoma, Uncinaria and Bunostomum spp.).

Of the blood feeding nematodes the genus Haemonchus causes anaemia and weight loss and if untreated frequently leads to death. Animals infected with the related non-blood feeding nematode Ostertagia similarly fail to thrive and may die if untreated.

Other parasitic worms of economic importance include the various species of the following helminth genera:—

Trichostrongylus, Nematodirus, Dictvocaulus, Cooperia, Ascaris, Dirofilaria, Trichuris and Strongylus. In addition to domestic livestock, companion animals and humans may also be infected, not infrequently with fatal results and helminth infections and infestations thus pose a problem of considerable worldwide significance.

Control of helminth parasites of grazing livestock currently relies primarily on the use of anthelmintic drugs combined with pasture management. Such techniques are often unsatisfactory, firstly because anthelmintic drugs may have to be administered frequently, secondly because resistance against anthelmintic drugs is becoming increasingly widespread and thirdly because appropriate pasture management is often not possible on some farms and even where it is, it can place constraints on the best use of available grazing.

Numerous attempts have been made to control helminth parasites of domestic animals by immunological means. With very few exceptions (e.g. the cattle lungworm, *Dictyocaulus viviparus*) this has not proved possible.

A vaccine against *F. hepatica* has been proposed in WO90/08819 comprising a glutathione-S-transferase from *F. hepatica* as antigenic material. Further vaccines against *F. hepatica* have been proposed in WO94/09142, WO94/28925 and PCT/GB95/02350 comprising respectively a Cathepsin L, a dipeptidyl peptidase and a class of haemoproteins from *F. hepatica* as antigenic material.

Bennett (UK Patent No. 2169606B) extracted various antigens from Fasciola organisms by a process which separates antigens specific to the juvenile stage from antigens present throughout the juvenile and adult stages.

Furthermore crude in vitro excretory/secretory (E/S) products can under some circumstances confer immunity on rats (Rajasekariah et al, Parasitol. 79 (1979), p. 393–400).

It has now been found that animals vaccinated against *F. hepatica* using a relatively impure haemoprotein preparation, the pure counterpart of which is described in PCT/GB95/02350, produce antibodies against peroxiredoxin and β-tubulin molecules of fluke origin. This discovery opens up the possibility of vaccines against *F. hepatica* and other helminths based on the use of peroxiredoxin and/or β-tubulin molecules and/or corresponding proteins produced by other helminth parasites as antigens.

Accordingly an aspect of the present invention provides a vaccine composition for use in combating a parasitic infestation of helminths in a mammal wherein the antigenic material comprises a peroxiredoxin and/or a β-tubulin molecule, in at least partially purified form, or an antigenic fragment or epitope, component, precursor, analogue, variant or functionally equivalent derivative thereof, together with a carrier and/or adjuvant.

The invention also provides a method of combating a parasitic infestation of helminths in a mammal comprising administering to said mammal a vaccine according to the invention as hereinbefore defined in an amount effective to combat said infestation.

Alternatively viewed, the invention provides for the use of the molecules as hereinbefore described in the preparation of a vaccine composition for combatting a parasitic infestation of helminths in a mammal.

The mammal is preferably a ruminant, for example cattle or sheep, but the vaccine and method of the invention may also find application in humans, companion animals such as dogs and cats or in other domestic animals.

Preferably the peroxiredoxin and/or β-tubulin molecules are derived from flukes such as Fasciola or Dicrocoelium, in particular from the liver fluke *Fasciola hepatica*. Alternatively it is preferred that the peroxiredoxin and/or β-tubulin molecules should be capable of stimulating an immune response which will be effective against Fasciola or Dicrocoelium, in particular *F. hepatica* and *F. gigantica*, such peroxiredoxin and/or β-tubulin molecules from other species as are capable of conferring a cross-protective immune response thus forming a particularly preferred aspect of the invention.

The *F. hepatica* peroxiredoxin and β-tubulin molecules shown hereinafter to possess cDNA sequences and predicted amino acid sequences as shown in FIGS. 2 and 4 respectively are particularly preferred for use in the vaccine and method of the invention.

The peroxiredoxin and/or β-tubulin molecules incorporated in the vaccine according to the invention are in at least partially purified form. Preferably the molecules of the present invention are at least 75% pure and more preferably at least 95% pure. It will be appreciated that once peroxiredoxin and/or β-tubulin molecules of at least 95% purity have been obtained they can be admixed with one or more further purified antigenic proteins, to form a polyvalent vaccine.

According to the present invention the peroxiredoxin and/or β-tubulin molecules incorporated in the vaccine may be in the form of antigens, antigenic fragments, epitopes, components, precursors, analogues or functionally-equivalent derivatives thereof.

A preferred form of polyvalent vaccine according to the invention will contain peroxiredoxin and/or β-tubulin polypeptides as referred to above in combination with a Cathepsin L-type antigen as described in more detail in International Patent Application No. WO94/09142 or a dipeptidyl peptidase antigen as described in more detail in International Patent Application No. WO94/28925 or a class of haemoprotein molecules as described in more detail in International Patent Application No. PCT/GB95/02350. Thus the Cathepsin L and/or dipeptidyl peptidase and/or haemoproteins are preferably derived from flukes such as Fasciola or Dicrocoelium, in particular the liver fluke *F. hepatica*. Such a polyvalent vaccine will, by inducing immunity in the host species against two or more separate aspects of the invading helminth parasite, significantly increase the likelihood of protection against the helminth and significantly reduce the chances of infestation occurring.

Monovalent vaccines according to the invention may also have an anti-fecundity effect on helminth parasites, and this effect should be still more marked with polyvalent vaccines.

In a preferred aspect the polyvalent vaccine comprises peroxiredoxin and/or β-tubulin polypeptides according to the present invention together with a Cathepsin L1 having molecular weight of 27 kDa by sodium dodecyl sulphate polyacrylamide gel electrophoresis as disclosed in WO94/09142 and/or a Cathepsin L2 having molecular weight of 29.5 kDa by the same technique as disclosed in WO94/09142 and/or a dipeptidyl peptidase having molecular weight of 200 kDa by the same technique as disclosed in WO94/28925 or one or more of a class of haemoproteins of at least 200 kDa by gel filtration chromatography as disclosed in PCT/GB95/02350.

The vaccines according to the invention may be formulated with conventional carriers and/or adjuvants and the invention also provides a process for the preparation of the vaccines comprising bringing into association purified peroxiredoxin and/or β-tubulin molecules as hereinbefore described and one or more adjuvants or carriers. Suitable adjuvants include aluminium hydroxide, saponin (ISCOMs), quil A and more purified forms thereof, muramyl dipeptide, mineral and vegetable oils, DEAE dextran, nonionic block copolymers or liposomes such as Novasomes (Trade Mark of Micro Vesicular Systems Inc.), in the presence of one or more pharmaceutically acceptable carriers or diluents. Carriers for peptide sequences corresponding to epitopes of peroxiredoxin or β-tubulin molecules according to the invention can be proteins such as Hepatitis B core antigen multiple antigen peptide or lipopeptides such as tripalmitoyl-S-glycerylcysteinylserylserine ($P_3CSS$). Suitable diluents include liquid media such as saline solution appropriate for use as vehicles. Additional components such as preservatives may be included.

Administration of the vaccine to the host species may be achieved by any of the conventional routes, e.g. orally or parenterally such as by intramuscular injection, optionally at intervals e.g. two injections at a 7–35 day interval. A suitable dose when administered by injection might be such as to give an amount of protein within the range 10–500 $\mu$g.

According to a further aspect, the invention provides the *F. hepatica* peroxiredoxin molecule or antigenic fragments, epitopes, components, precursors, analogues or variants thereof and functionally-equivalent derivatives thereof having protective antigenic activity against one or more helminth parasites, characterised by:
(a) having at least a portion which substantially corresponds to the amino acid sequence as shown in FIG. 4;
(b) being encoded by a nucleotide sequence at least a portion of which substantially corresponds to the sequence shown in FIG. 4;

While the peroxiredoxin and/or β-tubulin molecules for use in the vaccine according to the invention may be prepared by isolation from the helminths, it may also be convenient to prepare them by recombinant DNA techniques with the known advantages which such techniques give in terms of scaling-up of production and reproducibility. Thus the invention also provides for peroxiredoxin and β-tubulin molecules as hereinbefore described, produced by means of recombinant DNA techniques.

Accordingly, in one aspect, the present invention provides for nucleic acid sequences which encode the peroxiredoxin or the β-tubulin molecules of the invention or antigenic portions thereof substantially corresponding to all or a portion of the nucleotide sequences as-shown in FIG. 4 for peroxiredoxin and FIG. 2 for β-tubulin or sequences encoding helminth peroxiredoxin or β-tubulin antigens which are substantially homologous or which hybridise with any of said sequences.

A nucleic acid according to the invention may thus be single or double stranded DNA, cDNA or RNA.

Variations in the peroxiredoxin or β-tubulin-encoding nucleotide sequences may occur between different strains of helminth within a species, between different stages of a helminth life cycle (e.g. between larval and adult stages), between similar strains of different geographical origin, and also within the same helminth. Such variations are included within the scope of this invention.

"Substantially homologous" as used herein includes those sequences having a sequence identity of approximately 50% or more, eg. 60% or more, and also functionally-equivalent allelic variants and related sequences modified by single or multiple base substitution, addition and/or deletion. By "functionally equivalent" is meant nucleic acid sequences which encode polypeptides having anti-oxidant or β-tubulin functionality which are similarly immunoreactive i.e. which raise host protective antibodies against helminths.

Nucleic acid molecules which hybridise with the sequences shown in FIGS. 2 and 4 or any substantially homologous or functionally equivalent sequences as defined above are also included within the scope of the invention. "Hybridisation" as used herein defines those sequences binding under non-stringent conditions (6×SSC/50% formamide at room temperature) and washed under conditions of low stringency (2×SSC, room temperature, more preferably 2×SCC, 42° C.) or conditions of higher stringency eg. 2×SSC, 65° C. (where SSC=0.15M NaCl, 0.015M sodium citrate, pH 7.2).

Methods for producing such derivative related sequences, for example by site-directed mutagenesis, random mutagenesis, or enzymatic cleavage and/or ligation of nucleic acids are well known in the art, as are methods for determining whether the thus-modified nucleic acid has significant homology to the subject sequence, for example by hybridisation.

Provision of a nucleic acid molecule according to the invention thus enables recombinant peroxiredoxin or $\mu$-tubulin or immunogenic fragments thereof, to be obtained in quantities heretofore unavailable, thereby permitting the development of anti-helminth vaccines.

In another aspect the present invention thus provides nucleic acid molecules comprising one or more nucleotide sequences encoding one or more polypeptides capable of raising protective antibodies against helminth parasites, which sequences incorporate one or more antigenic determinant-encoding regions from the peroxiredoxin or β-tubulin encoding sequences as shown in FIGS. 2 and 4.

The present invention also extends to synthetic polypeptides comprising one or more amino acid sequences constituting a peroxiredoxin or β-tubulin molecule or antigenic portions thereof, substantially corresponding to all or a portion of the nucleotide sequences as shown in FIGS. 2 and 4 or a functionally-equivalent variant thereof.

Additional aspects of the invention related to the above include vectors containing one or more nucleotide sequences as defined above; host cells, for example bacteria such as *E. coli* or yeast cells such as Saccharomyces spp., or more preferably eukaryotic cells, transformed by such vectors, for example by a baculovirus vector; and processes for preparing recombinant peroxiredoxin and β-tubulin polypeptides or antigenic fragments or epitopes thereof comprising culturing such transformed host cells and isolating said peroxiredoxin or β-tubulin polypeptides or fragments or epitopes from the cultured cells.

An alternative live or inactivated vaccine formulation may comprise an attenuated or virulent virus or a host cell, e.g. a microorganism such as a bacterium, having inserted therein a nucleic acid molecule (e.g. a DNA molecule) according to the invention for stimulation of an immune response directed against polypeptides encoded by the inserted nucleic acid molecule. A bacterial vector which elicits local gut mucosal immunity to a fluke antigen which then blocks juvenile fluke migration is particularly preferred, notably invasive species such as Salmonella species.

Additional antigenic materials may also be present in the vaccine thus giving an enhanced protective effect against the helminth parasite in question or a combined protective effect against one or more additional parasitic infestations.

A yet further aspect of the invention provides monoclonal or polyclonal antibodies capable of inducing immunity to peroxiredoxin or β-tubulin molecules in a mammal when administered to said mammal, the antibodies having an affinity for the variable region of one or more further antibodies, said further antibodies having an affinity for said thiol-specific antioxidant or β-tubulin molecules.

This approach, the so-called "anti-idiotype" approach, permits formulation of a vaccine which will dispense entirely with the original antigen and may offer even greater advantages in terms of safety, avoidance of side effects and convenience of manufacture.

Figure 1:
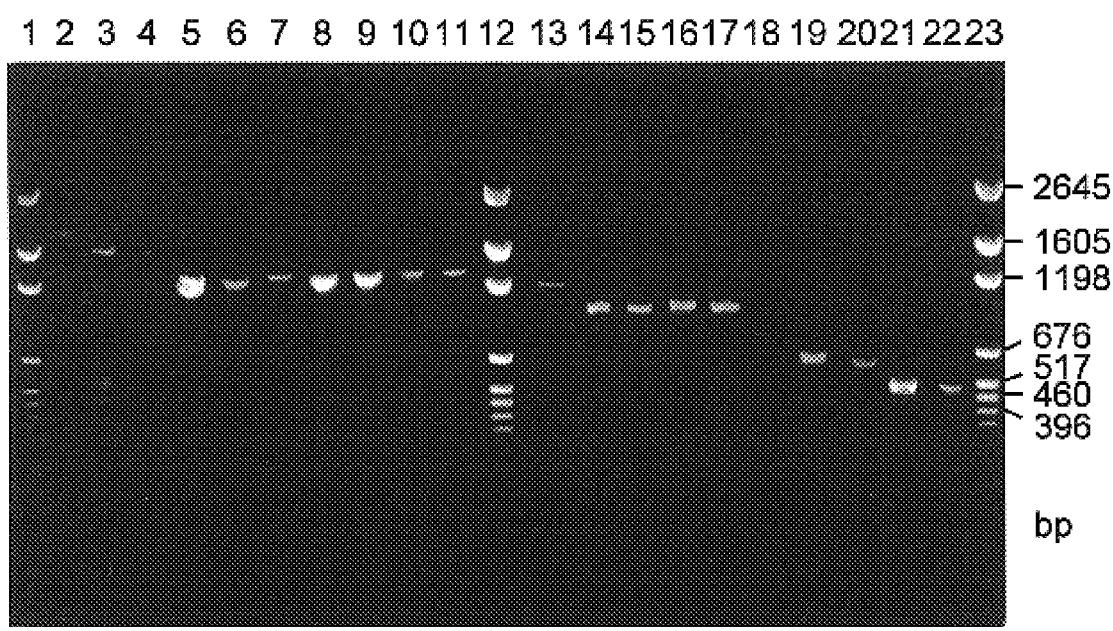
FIG. 1

PCR amplified inserts of immunoselected λ gt11 clones. Positive clones were amplified by PCR using universal λ forward and reverse primers. Samples of each PCR reaction were analysed by agarose gel electrophoresis.

| lanes 1, 12, 23 | pGem DNA markers | |
|---|---|---|
| lane 2 | clone | D6 |
| lanes 3 & 4 | clones | B5, D5 |
| lanes 5–11 | clones | A1, A4, A5, B1, B4, B6, E3 |
| lane 13 | clone | C4 |
| lanes 14–17 | clone | C2, D1, D7, E2 |
| lane 18 | clone | D8 |
| lanes 19 & 20 | clones | C1, D3 |
| lane 21 | clone | A8 |
| lane 22 | clone | E4 |

FIGS. 2A and 2B

Nucleotide sequence (SEQ ID NO:1) and deduced amino acid sequences (SEQ ID NOS: 2–6) of clone D6 (β-tubulin).

FIGS. 3A and 3B

Alignment of predicted amino acid sequence of clone D6 to Toxoplasma β-tubulin. The deduced amino acid sequence (SEQ ID NO:7) of the partial D6 sequence was aligned with that of β-tubulin from *Toxoplasma gondii* (SEQ ID NO:8 GenBank accession no. P10878, Nagel and Boothroyd, 1988). Boxes surround homologous regions and gaps have been introduced to give maximum alignment. Z=not determined.

FIG. 4

Nucleotide sequence (SEQ ID NO:10) and predicted amino acid sequence of (peroxiredoxin) (clone B1).

Figure 5A:
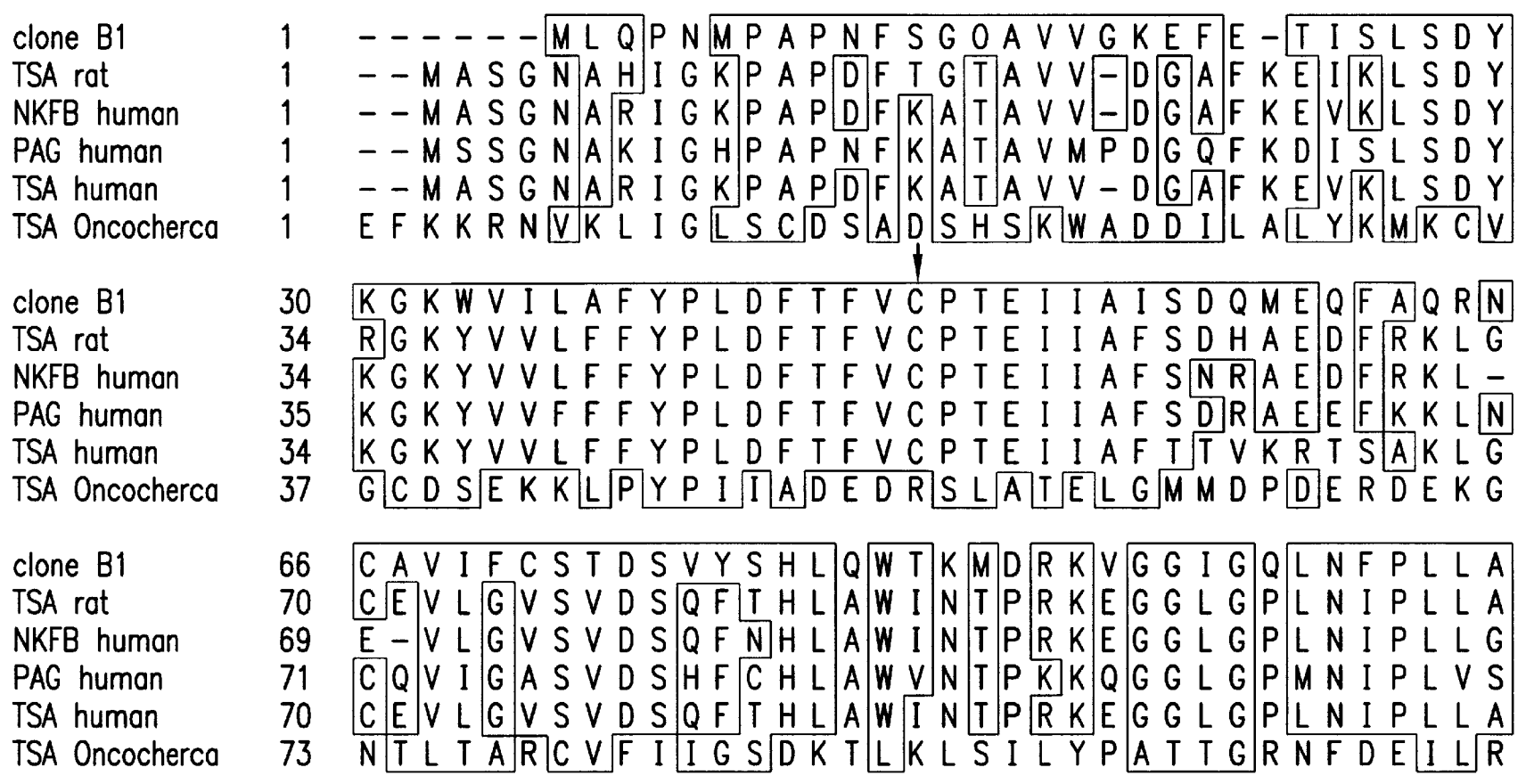

FIGS. 5A and 5B

Alignment of predicted amino acid sequence (SEQ ID NO:10) of clone B1. The deduced amino acid sequence of clone B1 was aligned with that of rat thiol-specific antioxidant (TSA, SEQ ID NO:11, GenBank accession no. P35704), human natural killer cell enhancing factor B, (NKEF B, SEQ ID NO:12, accession no. P31945), human proliferation associated gene, (PAG, SEQ ID NO:13, accession no. X67951), human TSA (SEQ ID NO:14, Lim et al, 1994, accession no. P35701), and *Onchocerca volvulus* TSA (SEQ ID NO:15, accession no. U09385). Boxes denote conserved residues and gaps have been introduced to maximise alignment. The active site cysteine residues are indicated by arrows.

FIG. 6

Expression of clone B1 fusion protein.

A. Plate wash supernatants of wild type phage (lane 1) and clone B phage (lane 2) were subjected to reducing SDS PAGE and silver staining.

B. Following electrophoresis, SDS gels were blotted onto nitrocellulose and probed with anti-β-galactosidase antibody. Lane 1 contains wild type phage supernatant and lane 2 contains clone B1 supernatant. Large arrows indicate the position of β-galactosidase. Small arrows indicate the position of B1 recombinant fusion protein.

FIG. 7

Northern blot analysis of total RNA from *F. hepatica* and bovine liver.

Total RNA from *F. hepatica* (lane 1) and from bovine liver (lane 2) was electrophoresed in a formaldehyde agarose gel, transferred to a nitrocellulose filter and probed with $^{32}p$ labelled 400 bp fragment. RNA size markers are indicated.

FIG. 8

Protection of glutamine synthetase by liver fluke homogenate against the DTT/$Fe^{3+}$ system. 0.5 U glutamine synthetase (GS) was incubated in the presence of the inactivating solution (IS): 15 μM $FeCl_3$ and 5 mM DTT, with 0.3 mg, 0.6 mg and 0.9 mg liver fluke homogenate (LFH), for 10 min at 37° C. Reactions were then assayed for remaining glutamine synthetase activity.

DETAILED DESCRIPTION OF THE INVENTION:

1. Materials

The Alpha $^{32}p$ dATP was obtained from Amersham, the RNAzol™ B from AMS Biotechnology Ltd., and the X-Omat X-ray film, FX 40 liquid Fixer, LX 24 developer 667 Polaroid film were all purchased from Kodak. Agarose, Anti-βgalactosidase antibody labelled with alkaline phosphatase (mouse), Apa I, 5-bromo-4-chloro-3-indolyl-β-D-galactosidase (X-Gal), dNTP's, EcoR I, Hind III, isopropylthio-β-D-galactoside (IPTG), pGem DNA markers, pGem® vector system, Prime-a-Gene® system, Sac I, Taq DNA Polymerase, WizarD™ λ preps, Wizard™ DNA clean-up system were all purchased from Promega. Adenine diphosphate (ADP), anti-bovine IgG conjugated to alkaline phosphatase (rabbit), diethylpyrocarbonate (DEPC), dithiothreitol (DTT), glutamine, glutamine synthetase, lysozyme, proteinase K, salmon sperm DNA all came from Sigma Chemical Company.

2. Immunoscreening of *F Hepatica* λ gt11 cDNA Expression Library

Preparation of λ gt11 cDNA Library

A λ gt11 cDNA Library was Prepared by the following standard method (Promega Handbook). Total RNA was isolated from mature adult flukes using RNAzoL™. From this, mRNA was isolated by binding to an oligo dT column. Double stranded cDNA was generated from the mRNA using the Riboclone® cDNA synthesis kit. EcoR I linker arms were added to the cDNA, which was then ligated to gt11 arms and packaged into λ heads using the Packagene® system. The packaged phage was titred and then amplified by infecting phage competent *E. coli* Y1090 cells (overnight culture grown in LB media with 0.2% maltose and 10 mM $MgSO_4$) with dilutions of the phage, incubating at room temperature for 20 min and then plating the bacteria in top agar onto LB agar plates with 100 μg ml$^{-1}$ ampicillin.

Preparation of Haemoglobin Fraction

Mature *F. hepatica* flukes were removed from the bile ducts of infected livers from condemned cattle at a local abattoir in Ireland. The flukes were washed six times in phosphate buffered saline (PBS), pH 7.3, and then maintained in RPMI-1640, pH 7.3, containing 2% glucose, 30 mM HEPES and 25 mg ml$^{-1}$ gentamycin at 37° C. for 18 hours. Following this incubation period the culture medium was removed, centrifuged at 12,000×g for 30 minutes and the supernatant (ES products) collected and stored at −20° C.

Five hundred ml of ES products were concentrated to 15 ml in an Amicon 8400 Ultrafiltration unit (Danvers, Mass., USA) with a YM3 membrane (3,000 mw cut-off). The concentrated sample was centrifuged at 12,000×g for 30 minutes and applied to a 340 ml Sephacryl S-200 column equilibrated in 0.1M Tris-HCl, pH 7.0, at 40° C. Fractions (5 ml) were collected after the void volume (110 ml) had been passed. The absorbance of the eluate was monitored at 280 nm using an Atto UV Monitor. Those fractions containing haemoprotein (yellow coloured) were pooled and concentrated in an Amicon 8050 Ultrafiltration unit to 5 ml. This concentrate was termed haemoglobin fraction (Hf).

Preparation of Sera for Immunoscreening

The cDNA library was immunologically screened using a pool of sera from animals vaccinated with haemoglobin fraction (Hf) as described above. The sera were obtained following three vaccinations with Hf and prior to parasite challenge. Before use the sera was pre-adsorbed to remove all antibodies reactive with *E. coli* proteins. This was achieved by incubating the sera with nitrocellulose discs containing bound *E. coli* proteins at room temperature for 6 h. This adsorption procedure was repeated three times. The discs were prepared by incubating the discs in a sonicated extract of *E. coli* cells (10×30 sec bursts, duty cycle 0.7 sec) for 24 h at 4° C. and then blocking the excess sites with 1% BSA/T-PBS. Sera was incubated with discs, removed, centrifuged and stored at 40° C. until required.

Immunoscreening of λ Library

Phage competent *E. coli* Y1090 were infected with 1:50 dilution of phage. Following an incubation for 20 min at room temperature the cells were plated in top agar on LB ampicillin plates and incubated at 42° C. until plaques were visible (ca 3 h). Nitrocellulose discs which had been soaked in 10 mM IPTG and air dried, were carefully placed on the plates and their orientation was marked by three needle stabs. The plates were incubated for 4 h at 37° C., the discs were then carefully removed and blocked overnight in 1% BSA/T-PBS, before probing with the pre-adsorbed bovine antisera (1:500 dilution). Following washing in T-PBS bound antibody was detected using alkaline phosphatase labelled anti-bovine IgG, with NBT and BCIP as substrate. Positive plaques appeared as purple rings. These plaques were removed as an agar plug using a sterile pasteur pipette, transferred to 1 ml phage buffer (10 mM $MgSO_4$, 100 mM NaCl, 20 mM Tris-HCl, pH 7.4) and allowed to diffuse at 4° C. overnight. Individual phage were re-plated and the antibody screening repeated two additional times or until pure plaques were obtained i.e. when all plaques on a plate were reactive with the antibody.

3. Preparation of λ Lysates and Isolation of DNA

Isolated plaques were picked into 200 μl 1.0×SM buffer (0.01% gelatin, 8 mM $MgSO_4$, 100 mM NaCl, 50 mM Tris-HCl, pH7.5) and incubated overnight at 4° C. One hundred μl was used to infect competent Y1090 cells, which were plated as before and incubated at 42° C. until confluent lysis was observed (ca 5 h). Four ml 0.1×SM buffer was added to the plate and after an overnight incubation at 4° C. the buffer was removed. Chloroform was added (0.5% final concentration) and the lysate was stored at 4° C. until required.

4. PCR Analysis of λ DNA

Polymerase Chain Reaction (PCR) was employed to isolate and estimate the size of the inserts from the phage library, using universal λ primers. These primers are derived from the sequence flanking the EcoR I cloning site of the λ gt11 vector. Twenty μl of stock λlysates was added to 180 μl water and boiled for 10 minutes and then 1 μl was used per 50 μl PCR. Each PCR vial consisted of the following mix:

| | |
|---|---|
| 10X Polymerase buffer | 5.0 μl |
| dNTP's (1 mM each) | 5.0 μl |
| $MgCl_2$ (25 mM) | 6.0 μl |
| Sterile distilled water | 30.7 μl |
| λ forward primer (50 ng μl$^{-1}$) | 1.0 μl |
| λ reverse primer (50 ng μl$^{-1}$) | 1.0 μl |
| Taq Polymerase (5 U μl$^{-1}$) | 0.3 μl |
| λ lysate DNA | 1.0 μl |

Each mix was overlaid with 70 μl mineral oil, placed in the Hybaid Omnigene Thermal Cycler, and the PCR carried out as follows:

| | | |
|---|---|---|
| Stage 1 | (Denaturation) | 94° C. for 4 min |
| Stage 2 | (Denaturation) | 94° C. for 30 sec |
| | (Annealing) | 55° C. for 1 min |
| | (Extension) | 74° C. for 1 min 30 sec |
| stage 2 was repeated for 35 cycles | | |
| Stage 3 | (Extension) | 74° C. for 4 min |

25 μl of PCR reactions were analysed by agarose gel electrophoresis as detailed in Sambrook et al (1989).

5. Sub Cloning of PCR Fragments

PCR amplified gene fragments were excised from the gel. The agarose was disrupted using glass beads, and the recovered DNA was purified using the Wizard™ DNA clean-up system (Promega). The fragments were then sub cloned directly into the pGem®-T plasmid, as follows:

1 μl (25 ng) pGem®-T vector, 8 μl ligase buffer (10 mM ATP, 100 mM $MgCl_2$, 100 mM DTT, 300 mM tris-HCl, pH 7.8), 1 U T4 DNA ligase and 100 ng insert DNA were mixed gently and the ligation was allowed to proceed overnight at 4° C.

Competent cells were prepared using one of the following methods:

(a) calcium chloride transformation A log phase culture of *E. coli* JM109 cells was aliquoted, placed on ice for 5 min, centrifuged at 12,000×g for 2 min and the supernatant removed. The cells were gently resuspended with 1 ml of cold CaCl$_2$ and incubated on ice for 30 min. The cells were spun again and resuspended in 0.5 ml cold CaCl$_2$. 10 μl ligation mix was carefully added to 50 μl aliquots of cells and placed on ice for a further 30 min. The cells were then heat shocked at 42° C. for 90 sec and returned to ice for 2–5 min. Immediately after transformation 950 μl pre-warmed LB media was added and the cells incubated at 37° C. for 1 h. Cells were concentrated by centrifugation and spread on LB plates containing 100 μg ml$^{-1}$ ampicillin, 0.5 mM IPTG and 40 μg ml$^{-1}$ X-Gal (for blue/white selection).

(b) electroporation

A log phase culture of *E. coli* XL1-blue electrocompetent cells was concentrated by centrifugation and aliquoted. 2.5 μl ligation reaction was added to 300 μl cells, gently mixed and placed in 0.2 μm electroporation cuvettes. The cells were then transformed by electroporating under the following conditions: the pulse generator was set at 25 μF, 2.48 kV, and 200 Ω. One pulse at these settings results in a pulse of 12.5 kV cm$^{-1}$ with a time constant of ca 4 sec. 1 ml pre-warmed SOC (containing 20 mM glucose) medium was added immediately and the cells were incubated for 1 h at 37° C., before concentrating and plating as before. Plates spread with transformed cells were incubated overnight at 37° C.

6. Screening of Recombinant Plasmids

With X-Gal and IPTG colour screening, recombinant colonies should be white and colonies with no insert DNA blue. White colonies were picked into 2 ml LB with 100 μg ml$^{-1}$ ampicillin (and 15 μg ml$^{-1}$ tetracycline for XL blue cells), and incubated overnight at 37° C. Plasmid DNA from 1 ml of this mini prep culture was isolated by either the boiling or alkali lysis method described by Sambrook et al (1989). The DNA was double digested with the restriction enzymes Sac I and Apa I and the inserts observed on agarose gel electrophoresis.

7. Sequencing of Plasmid DNA

Purified plasmid DNA from positive clones was further cleaned up using Wizard™ λ A preps. The DNA was sent for sequence analysis to the Department of Biological Sciences, Durham University or BioResearch Ireland, Trinity College Dublin.

8. Preparation of Fusion Protein

Sequence analysis revealed that clone B1 was a novel fluke antioxidant protein (peroxiredoxin) which was therefore further characterised. Fusion protein from the λ B1 clone was prepared by the plate wash supernatant method. Phage competent *E. coli* Y1090 were infected with 10,000 pfu recombinant phage and incubated for 20 min at room temperature, before pouring onto LB ampicillin plates in top agar. The plates were incubated at 42° C. for 3 h (lysis almost confluent), then 5 ml phage buffer containing 1 mM EDTA, 1 mM PMSF, 1 mM iodoacetamide and 10 mM IPTG was added to the plates which were incubated at 37° C. overnight. The buffer was recovered and the top agar was also scraped into a centrifuge tube. This was vortexed for 20 sec before centrifuging at 10,000×g for 10 min at 4° C. The supernatant was removed to microfuge tubes which were spun again at 12,000×g. Supernatants were stored at −20° C. until required.

The fusion protein was analysed by reducing SDS polyacrylamide gel electrophoresis followed by silver staining, and by immunoblotting using an anti-β galactosidase primary antibody.

9. Preparation of Radiolabelled DNA Probe

A 400 bp fragment was PCR amplified from clone B1 DNA using the following consensus primers, designed from comparing the protein sequences of the peroxiredoxin antioxidant family. These primers crossed the regions that code for the conserved active site regions, cys 47 (VCP 47) and cys 168 (VCP 168).

VCP 47 forward primer (Shem F)     (SEQ ID NO:16)
5' GAT TTY ACW TTY GTN TGT CCW ACW GAR -3'

VCP 168 reverse primer (SmTSAR)    (SEQ ID NO:17)
5' GGW CAN ACY TCW CCA TGY TC -3' where Y=T or C, W=A or G and N=T C, A or G

The PCR product was excised from an agarose gel and cleaned as before. The fragment was labelled with Alpha $^{32}$P by random priming using the Promega Prime-a-Genes® system. The reaction mix was as follows:

| | |
|---|---|
| 5X labelling buffer (250 mM tris-HCl, pH 8.0, 25 mM MgCl$_2$, 10 mM DTT, 1 mM HEPES, pH 6.6, 26 A$_{260}$ units ml$^{-1}$ random hexadeoxyribonucleotides) mixture of dCTP, dGTP, dTTP (100 mM each) | 10 μl |
| | 2 μl |
| acetylated BSA 10 mg ml-$^1$ | 2 μl |
| denatured DNA probe | 25 ng |
| sterile water | 25 μl |
| alpha $^{32}$P dATP (50 μCi, 3,000 Ci mMol$^{-1}$) | 5 μl |
| Klenow enzyme | 5 U |

The reaction tube was mixed gently and incubated at room temperature for 1 h. 200 μl 0.5 M EDTA was added and the reaction terminated by boiling for 2 min. The probe was now ready for use in hybridisation reactions.

10. Isolation of RNA and Northern Blotting a. Isolation of Adult Fluke RNA

Mature flukes were cultured overnight in RPMI-1640, pH 7.3 containing 2% glucose, 30 mM HEPES and 25 mg/l gentamycin, to allow clearing of the gut contents which could contain host cells. Approximately 10 flukes (1 gram tissue) were placed in a centrifuge tube, 5 ml RNAzol™ was added and the flukes were homogenised at top speed for 30 sec using a Thyristor Regler TR50 homogeniser. One ml of chloroform was added and the solution was shaken vigorously for 15 sec and placed on ice for 5 min. After aliquoting into microfuge tubes the solution was centrifuged at 13,000×g for 15 min at 4° C. and two layers formed. The upper aqueous phase was removed to a new tube, an equal volume of isopropanol was added and the samples were incubated at 40° C. for 15 min (or aliquoted for long term storage at −80° C.). They were recentrifuged for 15 min, the supernatant was removed and the RNA pellet washed with 75% ethanol before drying and reconstitution with 200 μl 0.1% DEPC treated water. Bovine RNA was isolated using the same procedure with 1 g fresh bovine liver as starting material. The RNA was analysed by electrophoresis on agarose gels containing formaldehyde as detailed in Sambrook et al (1989):

b. Northern Blotting

A Following electrophoresis the gel was rinsed with DEPC treated water to remove the formaldehyde and the RNA was transferred onto nitrocellulose membrane by the capillary transfer method outlined by Sambrook et al, (1989). RNA fragments are carried from the gel in a flow of buffer and deposited on the surface of the nitrocellulose. Following transfer, the RNA was fixed onto the membrane by baking for 2 h at 80° C. in an oven.

c. Hybridisation with Radiolabelled Probe

The nitrocellulose filter was soaked in 6×SSC (0.9 M NaCl, 90 mM sodium citrate pH 7.0) until thoroughly wetted and placed in a heat-sealable bag. Then, 200 ml prehybridisation solution (6×SSC, 5×Denhardt's reagent, 0.5% SDS, 100 μg ml denatured, fragmented salmon sperm DNA) was added to the bag. As much air as possible was squeezed from the bag which was sealed and incubated overnight at 68° C. Following incubation the bag was opened by removing a corner and the radiolabelled probe carefully added. The resealed bag was then placed in a second sealed bag and incubated again at 68° C. for 24 h. The hybridisation solution was carefully poured into a suitable container and the filters were removed and immediately submerged in 300 ml 2×SSC and 0.1% SDS. The filters were incubated with gentle agitation at room temperature for 15 min. The wash solution was replaced twice and the incubation repeated. Then 0.1×SSC and 0.5% SDS was added to the filters which were further incubated at 68° C. for 1 h. Filters were rinsed with 0.1×SSC to remove the SDS, blotted briefly on paper towels and wrapped in clingfilm, and then exposed to X-ray film at −80° C. to obtain an autoradiographic image. Exposure for 24 h at 80° C. with an intensifying screen was required to obtain an image.

11. Assay of Mature Fluke Extract for Novel Antioxidant Activity

Antioxidant activity in mature liver fluke extract was measured by monitoring its ability to inhibit the thiol/iron/oxygen mediated inactivation of glutamine synthetase. Assays were performed in microtitre plates in a 100 μl reaction volume containing 0.5 U glutamine synthetase (E. coli), in the presence or absence of inactivation solutions and protector protein (liver fluke homogenate). Inactivation solutions consisted of 15 μM $FeCl_3$ and either 5 mM DTT or 14 mM 2-mercaptoethanol (final concentrations). After incubation for 10 min at 37° C. remaining glutamine synthetase activity was measured by adding 100 μl of γ glutamyl transferase assay mixture. This contained 0.4 mM ADP, 150 mM glutamate, 10 mM potassium arsenate, 0.4 mM manganese chloride, 20 mM hydroxylammonium chloride in 50 mM imidazole-HCl, pH 7.0. The reaction was incubated at 37° C. for 30 min and terminated by the addition of 50 μl stop mixture, consisting of 55 g $FeCl_3.6H_2O$, 20 g trichloroacetic acid and 21 ml concentrated HCl per liter. An absorbance resulting from the γ glutamyl hydroxamate-$Fe^{3+}$ complex was measured at 540 nm. In the absence of "protector protein" under these conditions 70 to 100% of glutamine synthetase activity was lost.

12. Immunoscreening of F. hepatica cDNA Library and Analysis of Isolated Clones by PCR and Restriction Digestion Bovine sera from the vaccine trial was used to screen a F. hepatica cDNA library constructed in λgt11 phage. The serum pool used was obtained on the day of parasite challenge (week 11) from animals immunised with haemoglobin fraction (Hf). These animals showed a mean level of protection from parasite challenge of 43.8%. This sera should contain antibodies reactive with haemoglobin and any other antigens present in the immunising fraction.

Ten plates with ca 2,000 pfu on each were used in the primary screening with a 1:500 dilution of pre-adsorbed sera. Thirty positive plaques were chosen and these were subjected to three or four further rounds of screening until all plaques on the plates were positive indicating pure clones. Lysates of positive plaques were then prepared and the DNA analysed by PCR using λ forward and reverse primers. Of the thirty positives selected only twenty produced PCR products; the remaining ten were therefore disregarded. Clones were classified into groups on the basis of the size of the PCR fragment (FIG. 1).

| Group | Size of PCR fragment | Clones |
|---|---|---|
| 1 | ~1700 bp | D6 |
| 2 | ~1600 bp | B5 & D5 |
| 3 | ~1400 bp | A1, A4, A5, B1, B4, B6, E3 |
| 4 | ~1100 bp | C4 |
| 5 | ~1000 bp | C2, D1, D7, E2 |
| 6 | ~900 bp | D8 |
| 7 | ~700 bp | C1 & D3 |
| 8 | ~650 bp | A8 |
| 9 | ~550 bp | E4 |

13. Sub Cloning of Phage Inserts

Subcloning was performed with D6 of clone Group 1 (1700 bp) and B1 of Group 3 (1400 bp). The A PCR products of these two clones were subcloned directly into the pGem®-T plasmid. White colonies were picked and screened by double digestion with Sac I and Apa I restriction enzymes. A clone with a 1600–1700 bp insert was isolated from D6 and a 1400–1500 bp insert was obtained from clone B1.

14. Sequence Analysis of Clone D6

DNA from the recombinant plasmids was sequenced commercially following purification using Wizard™λ preps. From clone D6 a partial sequence of ca 420 bases was obtained. The deduced 141 amino acid sequence was compared to sequences from available databases and was found to show significant homology with the C-terminal end of β-tubulins from various organisms. β-tubulins are proteins of 440–450 amino acids in length, corresponding to ca 1320 bases, therefore clone D6 of ca 1700 bases may contain the entire F. hepatica βtubulin gene. FIG. 2 shows the alignment of the partial D6 sequence with β-tubulin from Toxoplasma gondii. In the region of overlap the D6 sequence shows 64% identity and 73% similarity with the C-terminus of the protozoan tubulin.

15. Sequence Analysis of Clone B1

Clone B insert was estimated to be ca 1400 bp in length by PCR amplification using λ primers. Approximately 1200 bases of the insert were sequenced in the 5' to 3' direction. This revealed a start codon ATG and an open reading frame of ca 580 bases ending with the in-frame termination codon TAG. Downstream from the termination codon was stretch of about 20 adenine residues (Poly A tail), preceded by two poly adenylation sequences, AAAATAAA (SEQ ID NO:18) and AATA (SEQ ID NO:19), indicating that the clone was complete at its 3' end. The DNA has a 5' untranslated region of ca 200 bases and a 3' untranslated region of ca 700 bases.

Clone B1 is predicted to encode a protein of 194 amino acids with a calculated molecular mass of 21,646 Da. When used to screen protein sequence databases, the predicted amino acid sequence shows a highly significant identity with a novel family of antioxidant proteins, the peroxiredoxin family. Alignment of clone B1 with rat thiol specific antioxidant (TSA, GenBank accession no. P35704), human natural killer cell enhancing factor B, (NKEF B, accession no. P31945), human proliferation associated gene, (PAG, accession no. X67951), human TSA (Lim et al, 1994, accession no. P35701), and Onchocerca volvulus TSA (accession no. 009385) is shown in FIG. 3.

The protein with the highest identity is rat TSA; 57.0% and 74.6% similar. The other identities are as follows human NKEF B 56.9%, (71.5% similar) human PAG 53.8% (73.0% similar), human TSA 53.7% (71.0% similar) and *Onchocerca volvulus* TSA 2.0% (33.7% similar). Similarity was observed over the entire length of the sequences and two highly conserved domains were observed. The first of these is a sixteen amino acid stretch at ca positions 40–60, FYPLDFTFVCPTEIIA (SEQ ID NO: 20). The second shorter domain HGEVCPA (SEQ ID NO: 21) is found at ca positions 165–175.

16. Expression of Fusion Protein by Clone B1

Figure 6A:
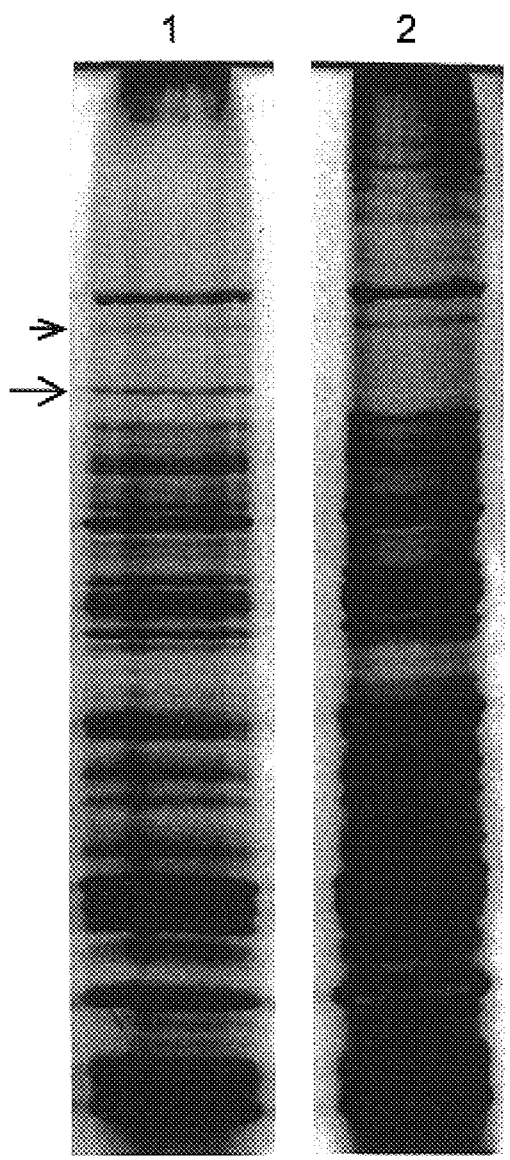
Figure 6B:
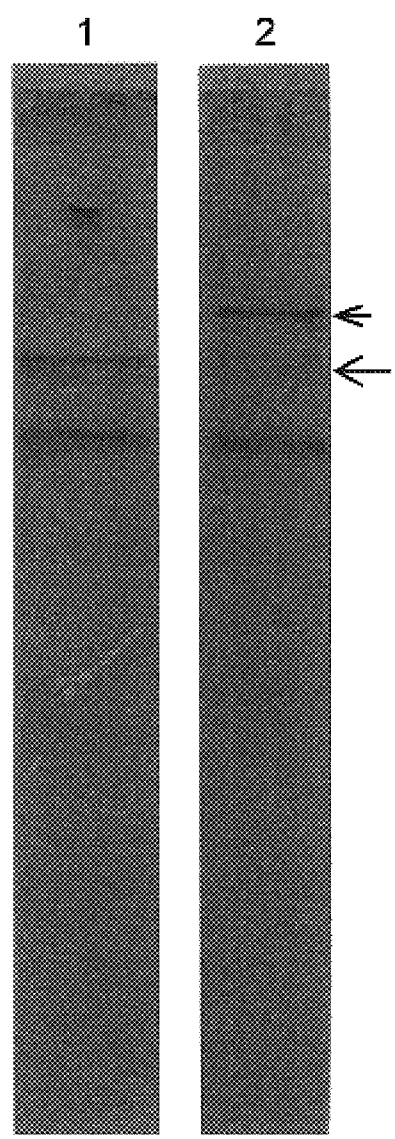

The plate wash supernatant method was used to make fusion proteins from clone B1 phage. The resulting supernatant and supernatant from *E. coli* infected with wild type phage were analysed on reducing SDS PAGE (FIG. 6A). In the wild type preparation a protein with the same molecular mass as β-galactosidase was observed (lane 1). In B1 supernatants this protein was absent but a larger protein of molecular mass ca 160 kDa, not found in wild type, was observed (lane 2). To determine if this was the fusion protein, the gel was blotted onto nitrocellulose paper and probed with anti-β-galactosidase antibody (FIG. 6B). Binding of the antibody to the large protein confirmed its identity as a β-galactosidase fusion protein (lane 2). The antibody also bound the wild type β-galactosidase molecule (lane 1) and a number of other proteins common to both supernatants.

17. Northern Analysis

Figure 7:
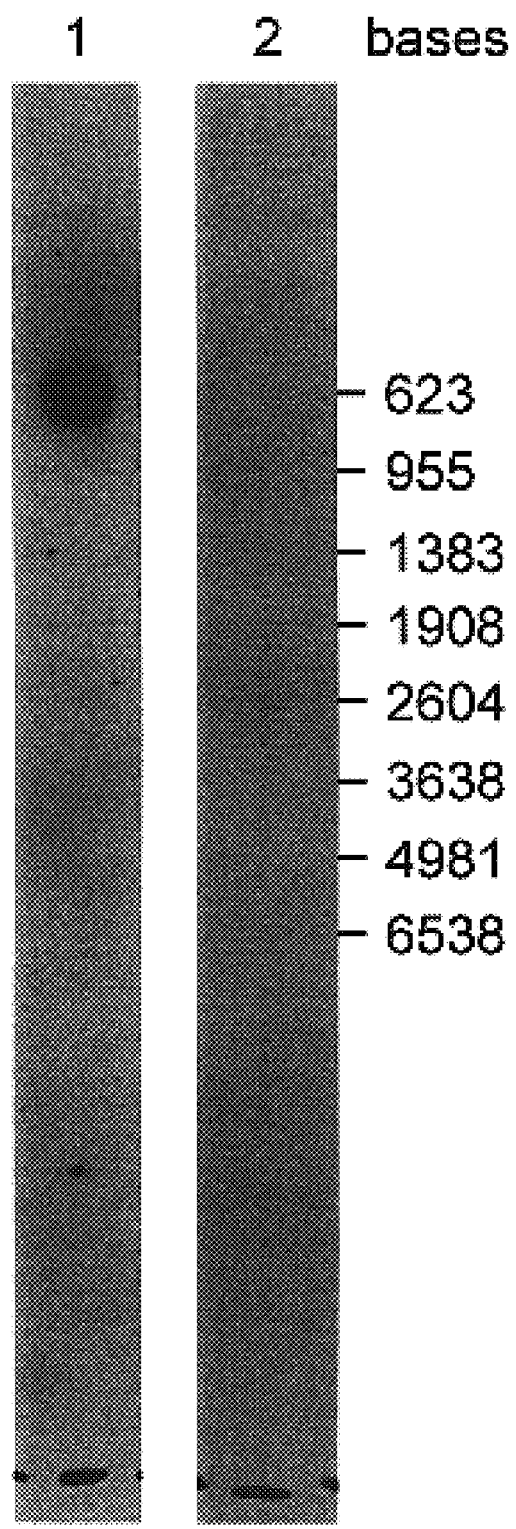

Primers designed from the conserved domains of the antioxidant proteins (around the VCP motifs at ca positions 50 & 170), were used to amplify a DNA fragment of ca 400 bp in length. This was $^{32}$P labelled and used to probe both *F. hepatica* and bovine RNA, which were analysed on an agarose gel prior to blotting. A single transcript of ca 750 kb was found in the *F. hepatica* RNA (FIG. 7 lane 1). No peroxiredoxin-similar binding was observed in the bovine RNA (FIG. 7 lane 2).

18. Antioxidant Activity of Mature Fluke Extract

Figure 8:
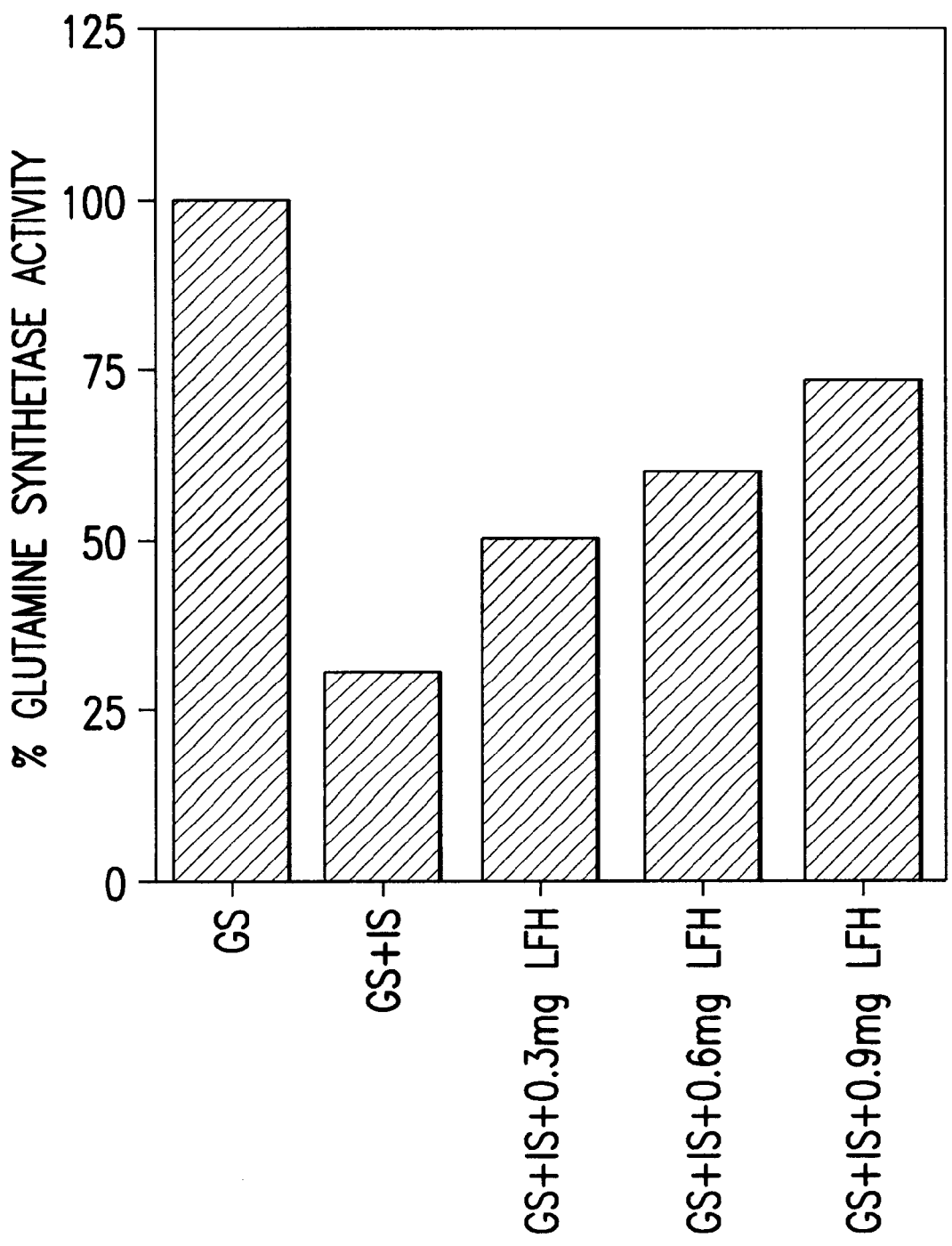

Antioxidant activity was measured as the ability of liver fluke extract to prevent the inactivation of glutamine synthetase by a mixed iron thiol inactivation system. FIG. 8 shows the inactivation of glutamine synthetase by iron and DTT in the presence of various levels of liver fluke homogenate (LFH). Incubation of glutamine synthetase with iron and DTT results in a 70% loss of the enzymes activity. The presence of LFH provides dose dependent protection, with 0.3 mg, 0.6 mg and 0.9 mg LFH restoring 50%, 61% and 75% glutamine synthetase activity, respectively.

BIBLIOGRAPHY

Lim., Y. S., Cha, M. K., Kim, H. K. and Kim, I. H. 1994. The thiol-specific antioxidant protein from human brain: gene cloning and analysis of conserved cysteine regions. Gene 140, 279–284.

Nagel, S. D. and Boothroy, J. C. 1988. The a and b tubulins of Toxoplasma gondii are encoded by single copy genes containing multiple copy introns. Molecular and Biochemical Parasitology 29, 261–273.

PCT/GB95/02350

Rajasekariah et al. (1979), Parasitology 79, 393–400.

Sambrook, J., Fritsch, E. F. and Maniatis, T. 1989. In Molecular Cloning: A Laboratory Manua. 2nd Ed. Cold Spring Harbour Laboratory Press.

UK Patent No. 2169606B

WO94/09142

WO94/28925

What is claimed is:

1. An isolated and purified protein comprising the amino acid sequence shown in SEQ ID NO:10.

2. A composition comprising an isolated protein having the amino acid sequence shown in SEQ ID NO:10 and at least one isolated protein having an amino acid sequence as shown in SEQ ID Nos: 2, 3, 4, 5 or 6.

* * * * *